United States Patent
Lee et al.

(10) Patent No.: US 10,147,891 B2
(45) Date of Patent: Dec. 4, 2018

(54) ORGANIC COMPOUND, ORGANIC OPTOELECTRONIC DEVICE, AND DISPLAY DEVICE

(71) Applicant: SAMSUNG SDI CO., LTD., Yongin-si, Gyeonggi-do (KR)

(72) Inventors: Han-Ill Lee, Suwon-si (KR); Ji-Hun Shin, Suwon-si (KR); Dong-Kyu Ryu, Suwon-si (KR); Eun-Sun Yu, Suwon-si (KR); Su-Jin Han, Suwon-si (KR); Jin-Seok Hong, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 8 days.

(21) Appl. No.: 15/110,258

(22) PCT Filed: Jul. 21, 2014

(86) PCT No.: PCT/KR2014/006609
§ 371 (c)(1),
(2) Date: Jul. 7, 2016

(87) PCT Pub. No.: WO2015/105251
PCT Pub. Date: Jul. 16, 2015

(65) Prior Publication Data
US 2016/0329506 A1     Nov. 10, 2016

(30) Foreign Application Priority Data
Jan. 9, 2014 (KR) .................. 10-2014-0003046

(51) Int. Cl.
*H01L 51/00* (2006.01)
*C07D 405/14* (2006.01)
(Continued)

(52) U.S. Cl.
CPC ........ *H01L 51/0073* (2013.01); *C07D 405/14* (2013.01); *C07D 409/14* (2013.01);
(Continued)

(58) Field of Classification Search
None
See application file for complete search history.

(56) References Cited

U.S. PATENT DOCUMENTS

| 6,821,643 B1 | 11/2004 | Hu et al. |
| 2007/0141387 A1 | 6/2007 | Nakano et al. |
| 2009/0026938 A1* | 1/2009 | Okada ................ H01L 51/5016 313/504 |

FOREIGN PATENT DOCUMENTS

| CN | 103232843 A | 8/2013 |
| CN | 103313980 A | 9/2013 |

(Continued)

OTHER PUBLICATIONS

Machine English translation of Kim et al. (KR 10-2012-0129733). Sep. 12, 2017.*

(Continued)

*Primary Examiner* — Jay Yang
(74) *Attorney, Agent, or Firm* — Lee & Morse, P.C.

(57) ABSTRACT

Disclosed are an organic compound represented by Chemical Formula 1, an organic optoelectronic device including the organic compound, and a display device including the organic optoelectronic device.

17 Claims, 1 Drawing Sheet

(51) Int. Cl.
*C07D 409/14* (2006.01)
*C09K 11/02* (2006.01)
*C09K 11/06* (2006.01)
*H01L 51/50* (2006.01)

(52) U.S. Cl.
CPC ............ *C09K 11/025* (2013.01); *C09K 11/06* (2013.01); *H01L 51/0067* (2013.01); *H01L 51/0074* (2013.01); *C09K 2211/1007* (2013.01); *C09K 2211/1059* (2013.01); *C09K 2211/1088* (2013.01); *C09K 2211/1092* (2013.01); *H01L 51/0081* (2013.01); *H01L 51/0085* (2013.01); *H01L 51/5016* (2013.01)

(56) References Cited

FOREIGN PATENT DOCUMENTS

| | | |
|---|---|---|
| JP | 2012-097006 A | 5/2012 |
| JP | WO2012/137958 A1 | 10/2012 |
| JP | 2013110262 A * | 6/2013 |
| JP | 2013-131518 A | 7/2013 |
| JP | WO 2012-157537 A | 7/2014 |
| KR | 10-2007-0030759 A | 3/2007 |
| KR | 10-2009-0130008 A | 12/2009 |
| KR | 10-2012-0031684 A | 4/2012 |
| KR | 10-2012-0129733 A | 11/2012 |
| KR | 10-2013-0011955 A | 1/2013 |
| KR | 10-2013-0078437 A | 7/2013 |
| WO | WO 2010/090077 A1 | 8/2010 |
| WO | WO 2012/099038 A1 | 7/2012 |
| WO | WO 2012/137958 A1 | 10/2012 |
| WO | WO 2013/027846 A1 | 2/2013 |
| WO | WO 2013/077352 A1 | 5/2013 |

OTHER PUBLICATIONS

Machine English translation of JP 2013-110262 A. Feb. 1, 2018.*
Chinese Office Action dated Dec. 20, 2017, of the corresponding Chinese Patent Application No. 201480072818.2.

* cited by examiner

[Fig. 1]
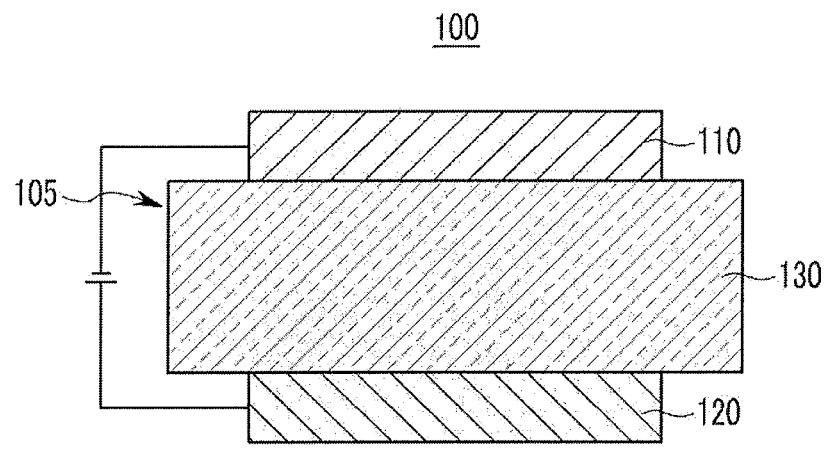
[Fig. 2]
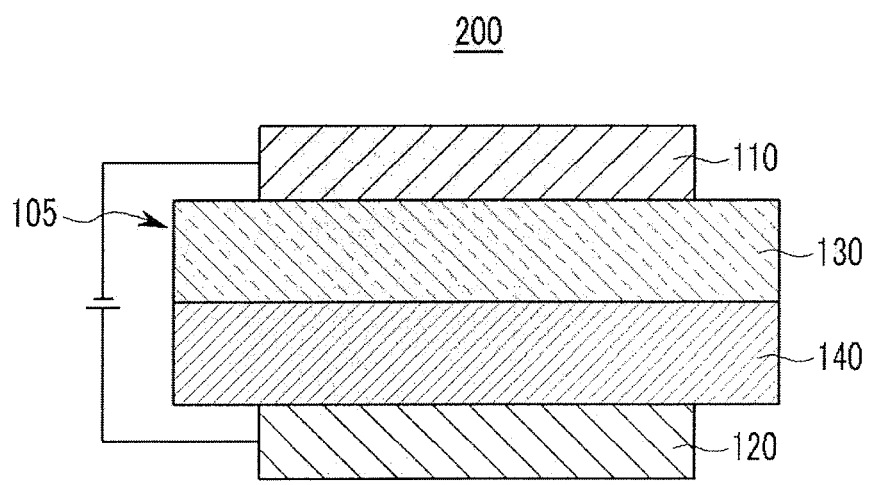

ORGANIC COMPOUND, ORGANIC OPTOELECTRONIC DEVICE, AND DISPLAY DEVICE

CROSS REFERENCE TO RELATED APPLICATIONS

This is the U.S. national phase application based on PCT Application No. PCT/KR2014/006609, filed Jul. 21, 2014, which is based on Korean Patent Application No. 10-2014-0003046, filed Jan. 9, 2014, the entire contents of all of which are hereby incorporated by reference.

TECHNICAL FIELD

An organic compound, an organic optoelectronic device, and a display device are disclosed.

BACKGROUND ART

An organic optoelectronic device is a device that converts electrical energy into photoenergy, and vice versa.

An organic optoelectronic device may be classified as follows in accordance with driving principles. One is an optoelectronic device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, an organic photo conductor drum, and the like.

Of these, an organic light emitting diode (OLED) has recently drawn attention due to an increase in demand for flat panel displays. The organic light emitting diode converts electrical energy into light by applying current to an organic light emitting material and has a structure in which an organic layer is interposed between an anode and a cathode. Herein, the organic layer may include an emission layer and optionally an auxiliary layer, and the auxiliary layer may be, for example at least one selected from a hole injection layer, a hole transport layer, an electron blocking layer, an electron transport layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Object

One embodiment provides an organic compound capable of realizing an organic optoelectronic device having high efficiency and long life-span.

Another embodiment provides an organic optoelectronic device including the organic compound.

Yet another embodiment provides a display device including the organic optoelectronic device.

Technical Solution

According to one embodiment, an organic compound represented by Chemical Formula 1 is provided.

[Chemical Formula 1]

In Chemical Formula 1, $X^1$ and $X^2$ are independently S, O, SO, or $SO_2$, $L^1$ and $L^2$ are independently a single bond or a C6 to C20 substituted or unsubstituted arylene group, Z is independently N, C, or $CR^a$, at least one of Z is N, $R^1$ to $R^{12}$ and $R^a$ are independently hydrogen, deuterium, a substituted or unsubstituted C1 to C20 alkyl group, a substituted or unsubstituted C6 to C20 aryl group, or a combination thereof, and n1 and n2 are independently 0 or 1.

According to another embodiment, an organic optoelectronic device includes an anode and a cathode facing each other, at least one organic layer between the anode and the cathode, wherein the organic layer includes the organic compound.

According to yet another embodiment, a display device including the organic optoelectronic device is provided.

Advantageous Effect

An organic optoelectronic device having high efficiency and long life-span may be realized.

DESCRIPTION OF DRAWINGS

FIGS. 1 and 2 are cross-sectional views of organic light emitting diodes according to one embodiment.

BEST MODE

Hereinafter, embodiments of the present invention are described in detail. However, these embodiments are exemplary, the present invention is not limited thereto and the present invention is defined by the scope of claims.

In the present specification, when a definition is not otherwise provided, the term "substituted" refers to one substituted with a deuterium, a halogen, a hydroxyl group, an amino group, a substituted or unsubstituted C1 to C30 amine group, a nitro group, a substituted or unsubstituted C1 to C40 silyl group, C1 to C30 alkyl group, a C1 to C10 alkylsilyl group, a C3 to C30 cycloalkyl group, a C3 to C30 heterocycloalkyl group, a C6 to C30 aryl group, C6 to C30 heteroaryl group, a C1 to C20 alkoxy group, a fluoro group, a C1 to C10 trifluoroalkyl group such as a trifluoromethyl group, or a cyano group, instead of at least one hydrogen of a substituent or a compound.

In addition, two adjacent substituents of the substituted halogen, hydroxy group, an amino group, a substituted or unsubstituted C1 to C20 amine group, a nitro group, a substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heteroaryl group, C1 to C20 alkoxy group, fluoro group, C1 to C10 trifluoroalkyl group such as trifluoromethyl group and the like, or cyano group may be fused to form a ring. For example, the substituted C6 to C30 aryl group may be fused with another adjacent substituted C6 to C30 aryl group to form a substituted or unsubstituted fluorene ring.

In the present specification, when specific definition is not otherwise provided, "hetero" refers to one including 1 to 3 hetero atoms selected from N, O, S, P, and Si, and remaining carbons in one compound or substituent.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a substituent including all element of the cycle having p-orbitals which form conjugation, and may be monocyclic, polycyclic or fused ring polycyclic (i.e., rings sharing adjacent pairs of carbon atoms) functional group.

In the present specification, "heteroaryl group" may refer to aryl group including 1 to 3 hetero atoms selected from N, O, S, P, and Si and remaining carbons in one functional group. The heteroaryl group may be a fused ring where each ring may include the 1 to 3 heteroatoms.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, or a combination thereof, but are not limited thereto.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

Hereinafter, an organic compound according to one embodiment is described.

An organic compound according to an embodiment is represented by Chemical Formula 1.

[Chemical Formula 1]

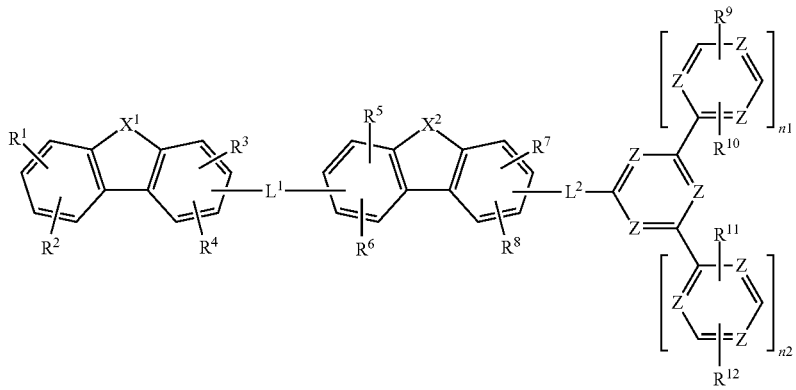

In Chemical Formula 1, $X^1$ and $X^2$ are independently S, O, SO, or $SO_2$, $L^1$ and $L^2$ are independently a single bond or a C6 to C20 substituted or unsubstituted arylene group, Z is independently N, C, or $CR^a$, at least one of Z is N, $R^1$ to $R^{12}$ and $R^a$ are independently hydrogen, deuterium, a substituted or unsubstituted C1 to C20 alkyl group, a substituted or unsubstituted C6 to C20 aryl group, or a combination thereof, and n1 and n2 are independently 0 or 1.

The organic compound represented by Chemical Formula 1 includes two fused heteroaryl groups including a sulfur atom (S), an oxygen atom (O), or a combination thereof and a heteroaryl group including at least one nitrogen. The two fused heteroaryl groups including a sulfur atom (S), an oxygen atom (O), or a combination thereof are moieties having hole characteristics, and the heteroaryl group including at least one nitrogen is a moiety having electron characteristics.

The organic compound may increase charge mobility due to the fused heteroaryl groups including sulfur atom (S), oxygen atom (O), or a combination thereof, and thus, decrease a driving voltage of organic optoelectronic device including the organic compound. The organic compound may increase a glass transition temperature (Tg) of a compound and may improve processability by enabling a relatively high temperature process by including the two fused heteroaryl groups including a sulfur atom (S), an oxygen atom (O), or a combination thereof.

The organic compound may have a structure of easily receiving electrons when an electric field is applied thereto due to the heteroaryl group including at least one nitrogen and thus, decrease a driving voltage of an organic optoelectronic device including the organic compound.

In addition, the organic compound has a bipolar structure by including both the moieties having hole characteristics and the moiety having electron characteristics, and may appropriately balance a flow of holes and electrons, and accordingly, improve efficiency of an organic optoelectronic device when applied thereto.

The organic compound has a linear structure wherein the two moieties having hole characteristics and the moiety having electron characteristics are sequentially arranged, and thereby may appropriately localize the moieties having hole characteristics and the moiety having electron characteristics and control a conjugation-system flow, and thus may have further improved bipolar characteristics. Accordingly, a life-span of an organic optoelectronic device including the organic compound may be improved.

The organic compound represented by Chemical Formula 1 may optionally have linking groups ($L^1$ and $L^2$) between the moieties having hole characteristics and/or the moiety having hole characteristics and the moiety having electron characteristics.

The $L^1$ and $L^2$ of Chemical Formula 1 may independently be a single bond or a C6 to C20 substituted or unsubstituted arylene group having a kink structure.

The kink structure is a structure that two linking moieties of the arylene groups is not a linear. For example, as for phenylene, ortho phenylene (o-phenylene) and meta phenylene (m-phenylene) have a kink structure where linking moieties do not form a linear structure, while para phenylene (p-phenylene) has no kink structure because where linking moieties form a linear structure.

When the $L^1$ and/or $L^2$ of Chemical Formula 1 is a C6 to C20 substituted or unsubstituted arylene group having a kink structure, it may be, for example a substituted or unsubstituted phenylene group having a kink structure, a substituted or unsubstituted biphenylene group having a kink structure, or a substituted or unsubstituted terphenylene group having a kink structure.

When the $L^1$ and/or $L^2$ of Chemical Formula 1 is a C6 to C20 substituted or unsubstituted arylene group having a kink structure, it may be, for example substituted or unsubstituted groups of Group 1, but is not limited thereto.

[Group 1]

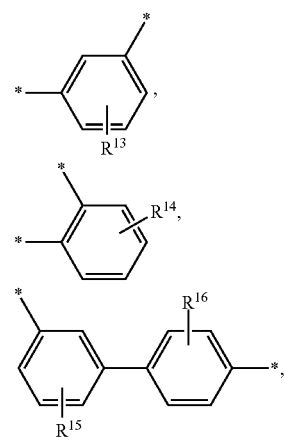

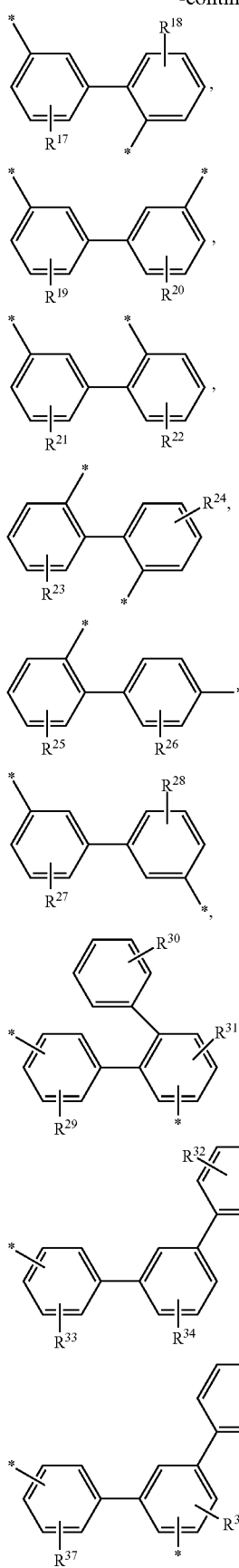

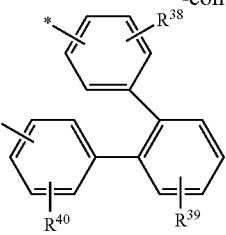

In Group 1,
R$^{13}$ to R$^{40}$ are independently hydrogen, deuterium, a substituted or unsubstituted C1 to C10 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a halogen, a halogen-containing group, a cyano group, a hydroxyl group, an amino group, a nitro group, a carboxyl group, a ferrocenyl group, or a combination thereof.

The organic compound represented by Chemical Formula 1 may be, for example represented by Chemical Formula 2 according to a bonding position.

[Chemical Formula 2]

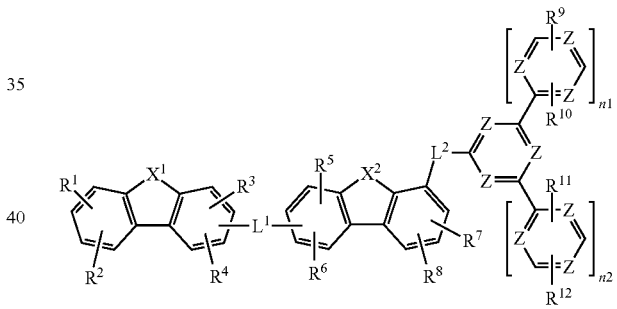

In Chemical Formula 2, X$^1$, X$^2$, L$^1$, L$^2$, Z, R$^1$ to R$^{12}$, n1, and n2 are the same as described above.

The organic compound represented by Chemical Formula 1 may be, for example represented by Chemical Formula 3 according to a bonding position.

[Chemical Formula 3]

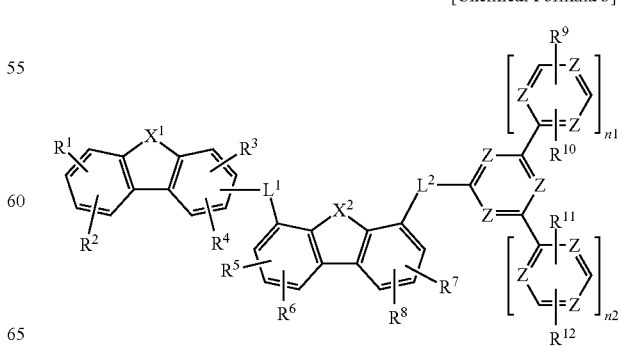

In Chemical Formula 3, $X^1$, $X^2$, $L^1$, $L^2$, Z, $R^1$ to $R^{12}$, n1, and n2 are the same as described above.

The organic compound represented by Chemical Formula 3 may be, for example represented by Chemical Formula 3a or 3b according to a bonding position.

[Chemical Formula 3a]

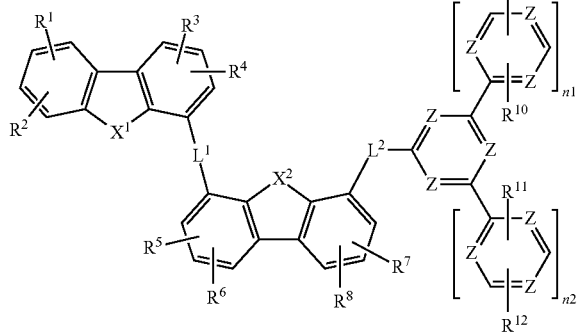

[Chemical Formula 3b]

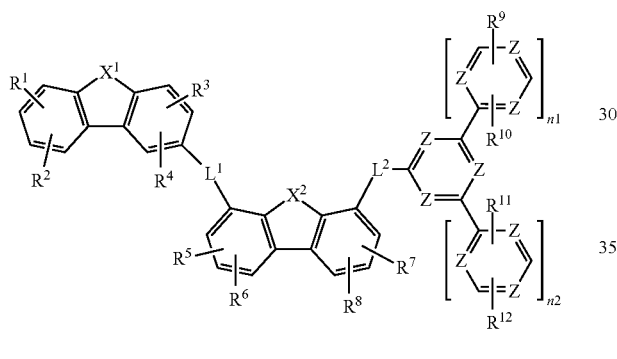

In Chemical Formulae 3a or 3b, $X^1$, $X^2$, $L^1$, $L^2$, Z, $R^1$ to $R^{12}$, n1, and n2 are the same as described above.

The organic compound represented by Chemical Formula 3a may be, for example represented by Chemical Formula 3aa and the organic compound represented by Chemical Formula 3b may be, for example represented by Chemical Formula 3ba.

[Chemical Formula 3aa]

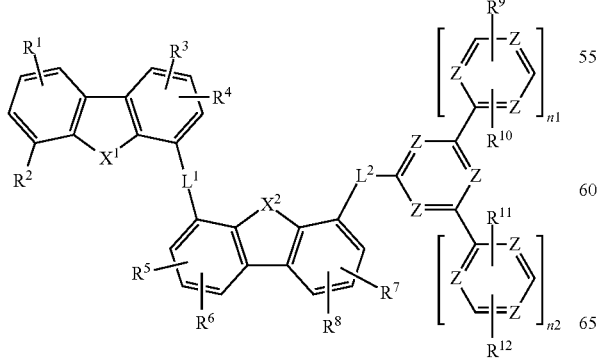

[Chemical Formula 3ba]

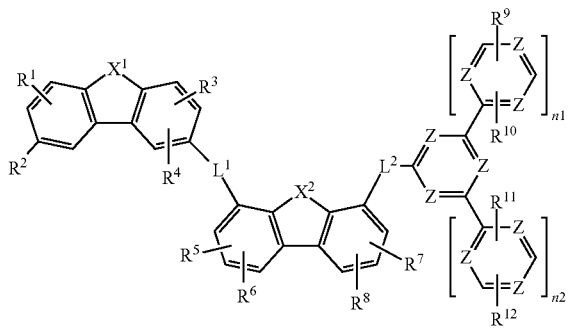

In Chemical Formula 3aa or 3ba, $X^1$, $X^2$, $L^1$, $L^2$, Z, $R^1$ to $R^{12}$, n1, and n2 are the same as described above.

In Chemical Formula 3aa or 3ba, $R^2$ having a fixed binding position may be, for example hydrogen or a substituted or unsubstituted C6 to C20 aryl group.

The organic compound represented by Chemical Formula 1 may be, for example represented by Chemical Formula 4 according to a bonding position.

[Chemical Formula 4]

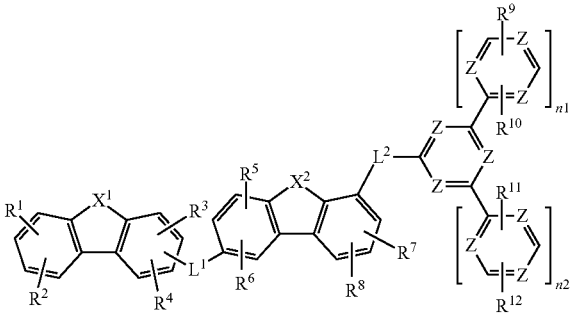

In Chemical Formula 4, $X^1$, $X^2$, $L^1$, $L^2$, Z, $R^1$ to $R^{12}$, n1, and n2 are the same as described above.

The organic compound represented by Chemical Formula 4 may be, for example represented by Chemical Formula 4a or 4b according to a bonding position.

[Chemical Formula 4a]

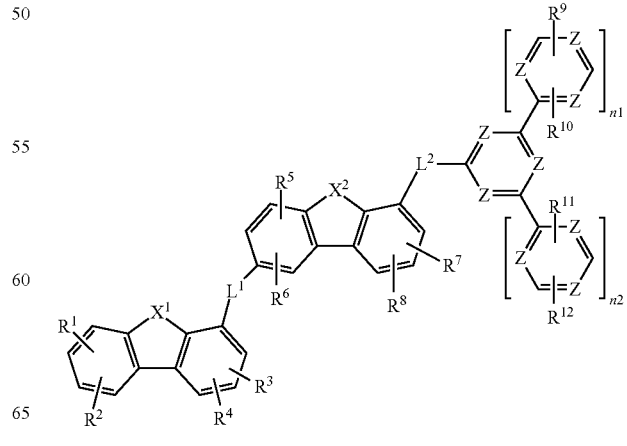

[Chemical Formula 4b]

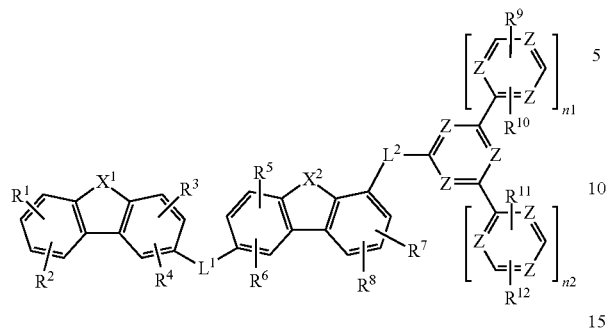

[Group 2]

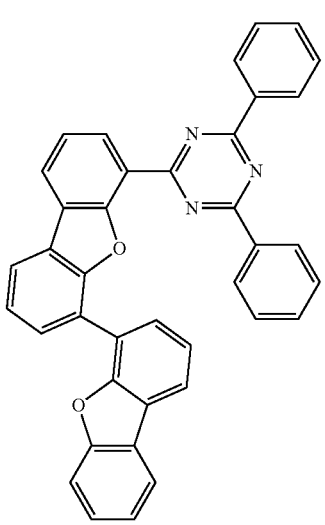

1

In Chemical Formulae 4a or 4b, $X^1$, $X^2$, $L^1$, $L^2$, Z, $R^1$ to $R^{12}$, n1, and n2 are the same as described above.

The organic compound represented by Chemical Formula 4a may be, for example represented by Chemical Formula 4aa and the organic compound represented by Chemical Formula 4b may be, for example represented by Chemical Formula 4ba.

[Chemical Formula 4aa]

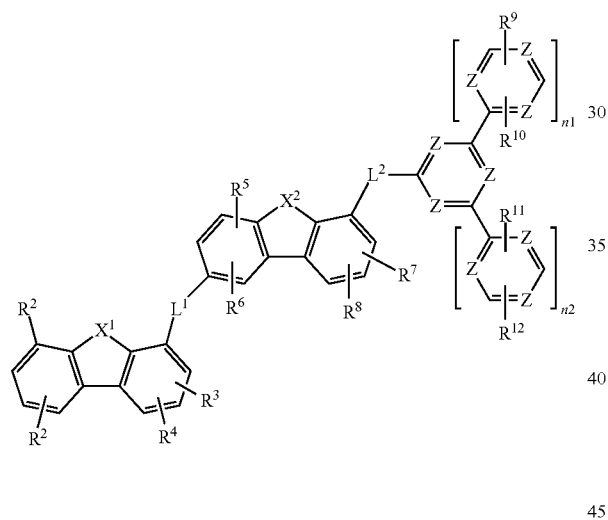

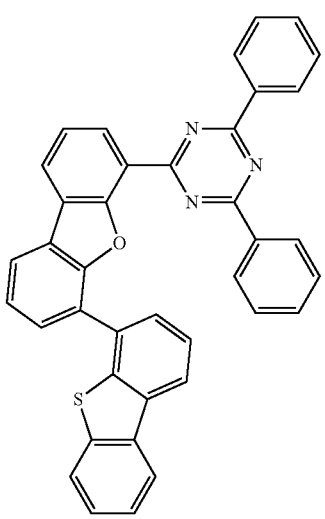

2

[Chemical Formula 4ba]

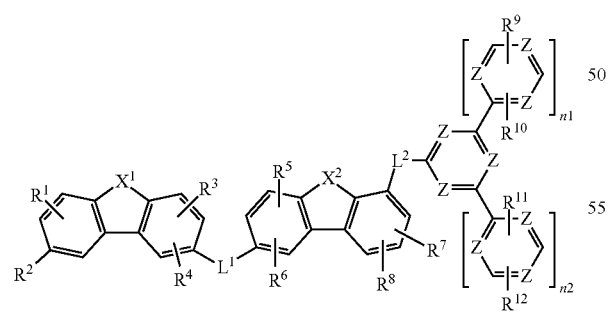

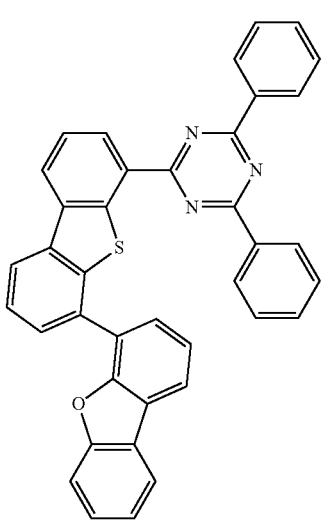

3

In Chemical Formulae 4aa or 4ba, $X^1$, $X^2$, $L^1$, $L^2$, Z, $R^1$ to $R^{12}$, n1, and n2 are the same as described above.

In Chemical Formulae 4aa or 4ba, $R^2$ having a fixed binding position may be, for example hydrogen or a substituted or unsubstituted C6 to C20 aryl group.

The organic compound may be, for example, compounds of Group 2, but is not limited thereto.

4
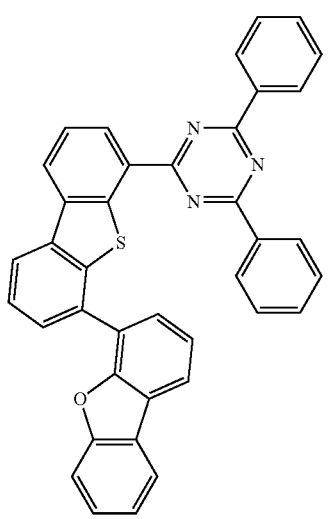
5
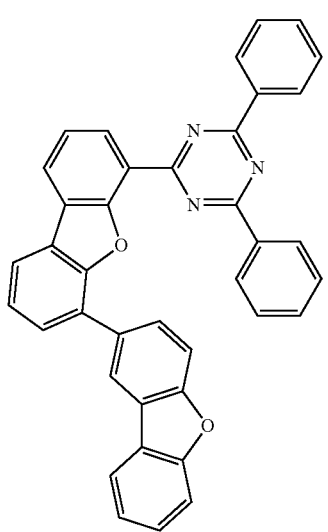
6
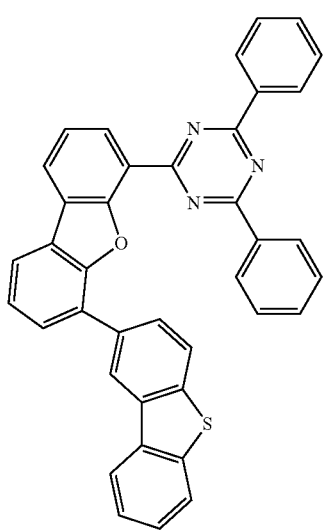
7
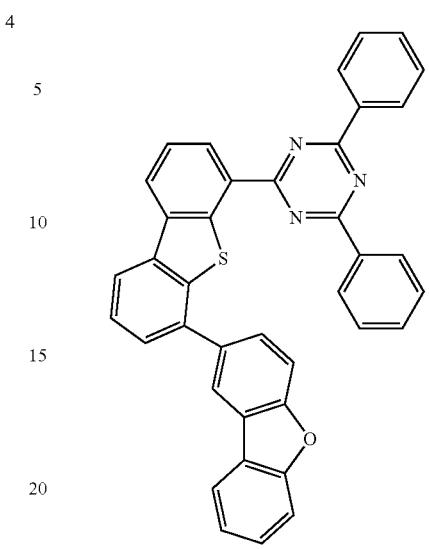
8
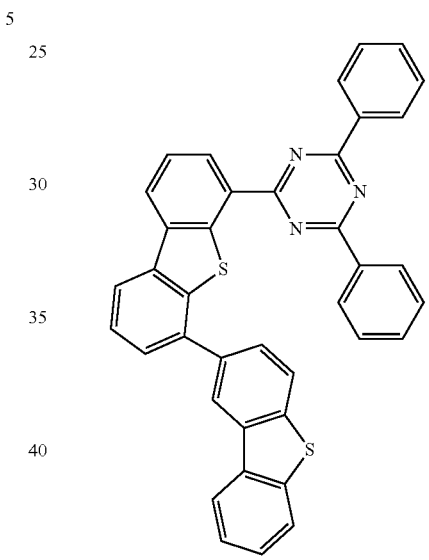
9
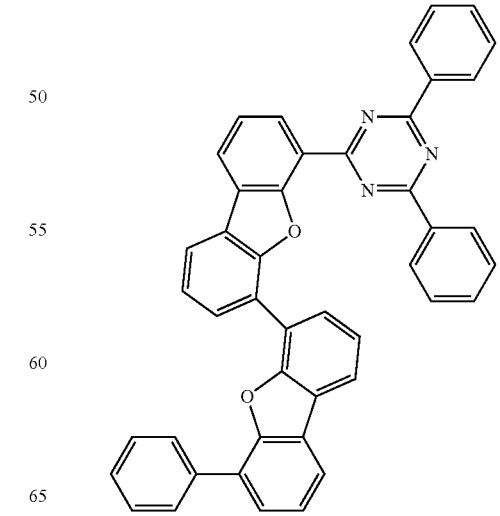

10
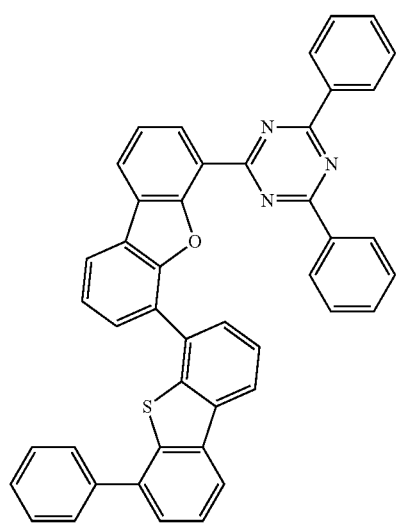
11
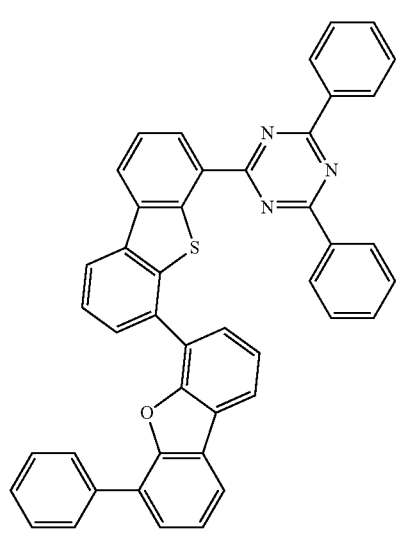
12
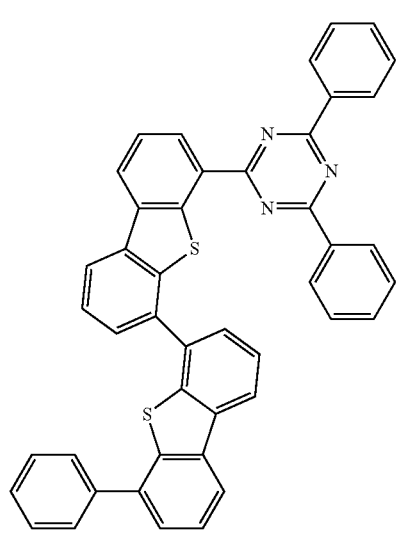
13
14
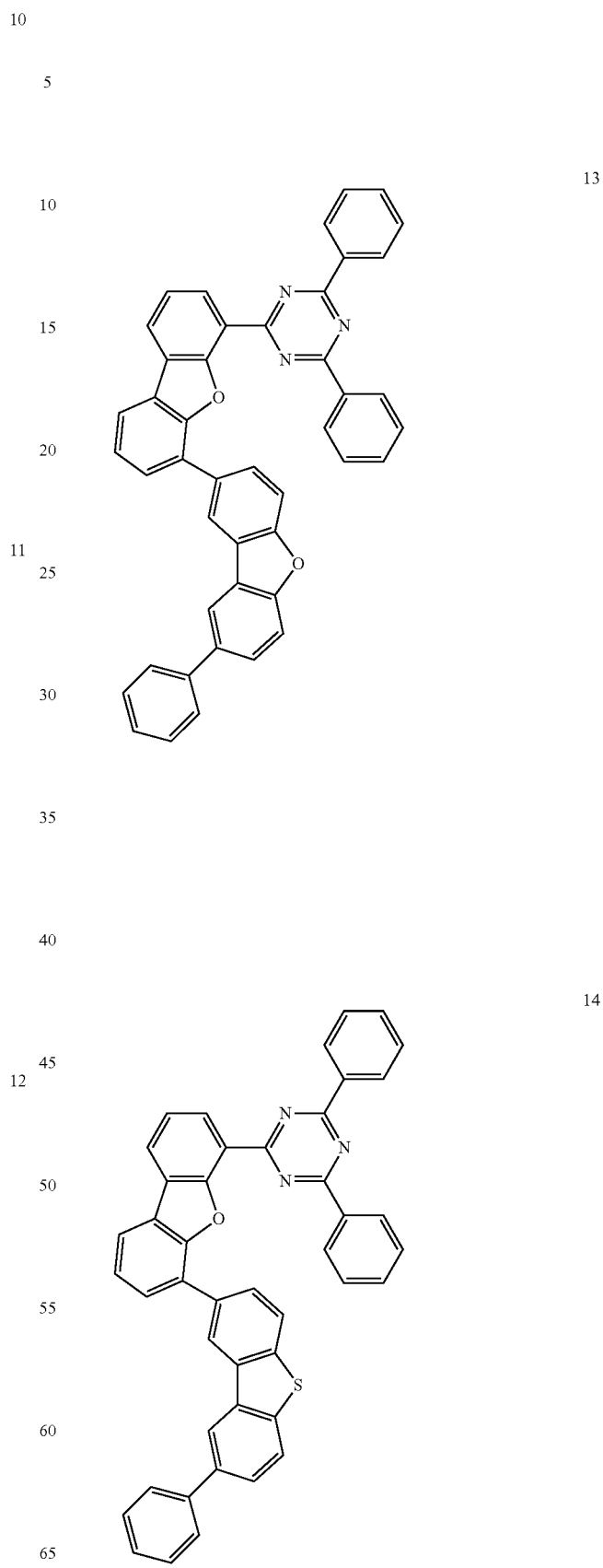

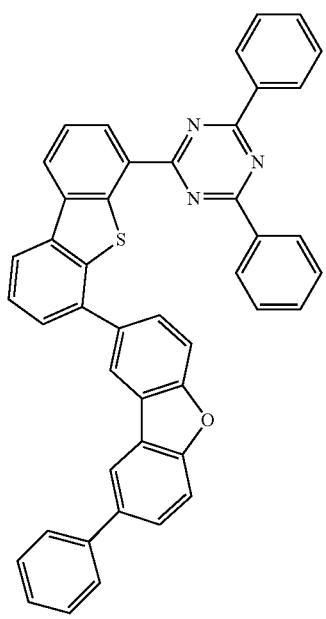
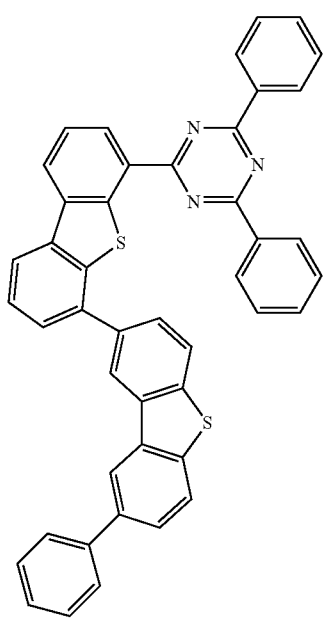
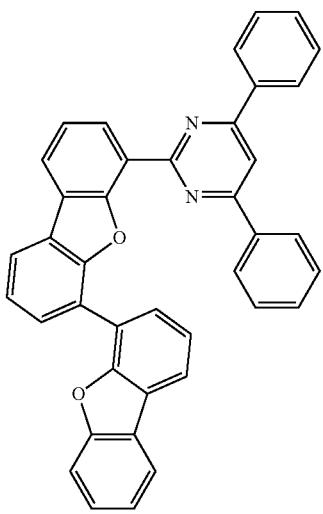
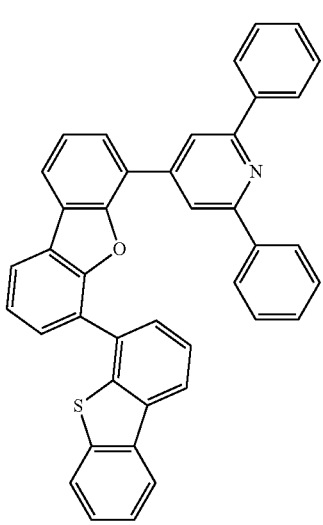
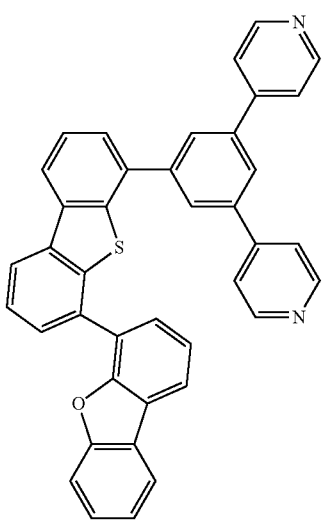

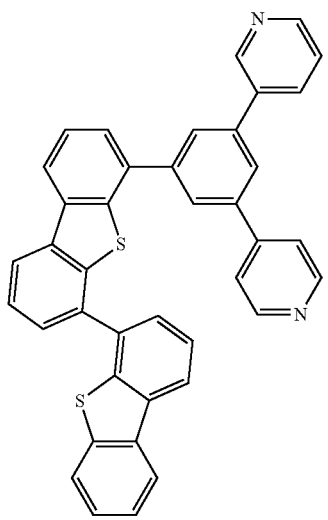
19
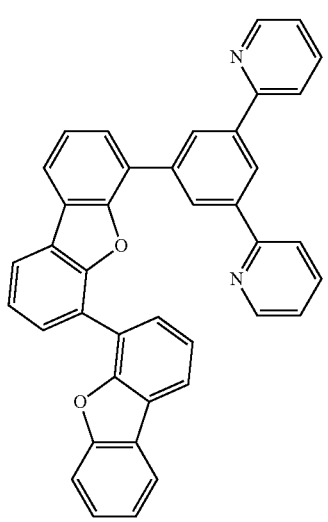
20
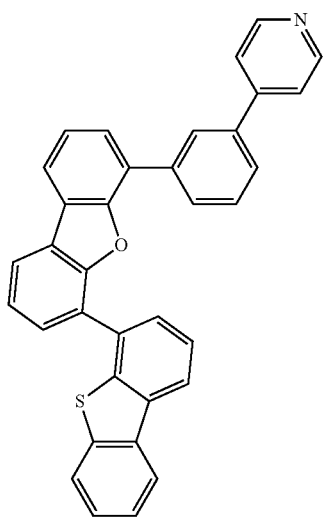
21
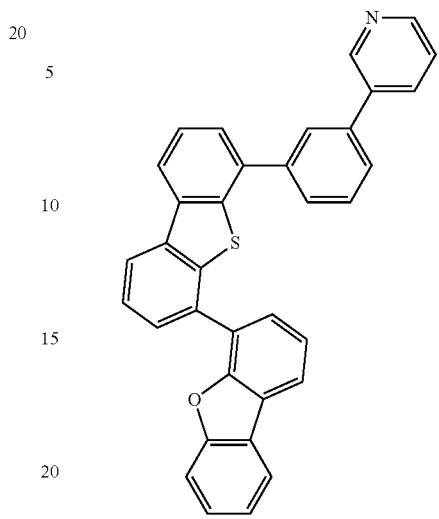
23
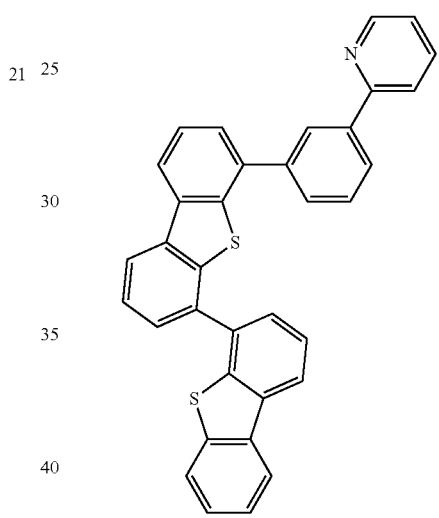
24
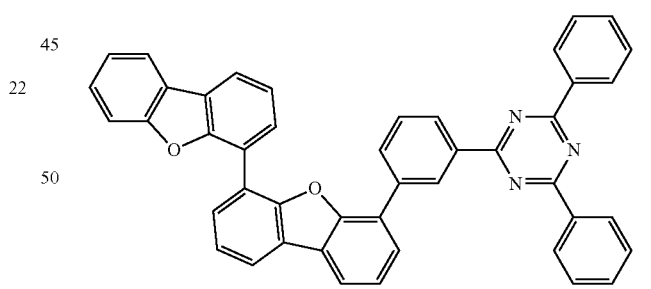
25
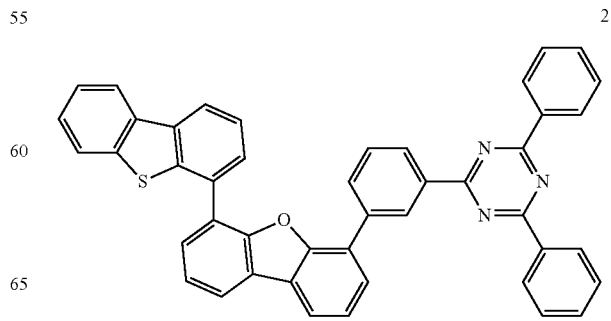
26

27
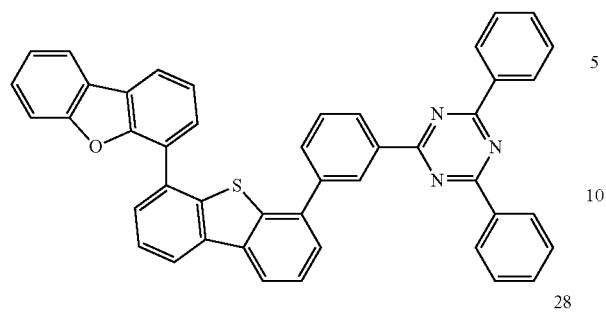
28
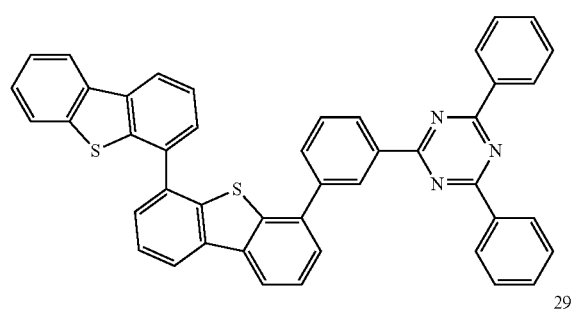
29
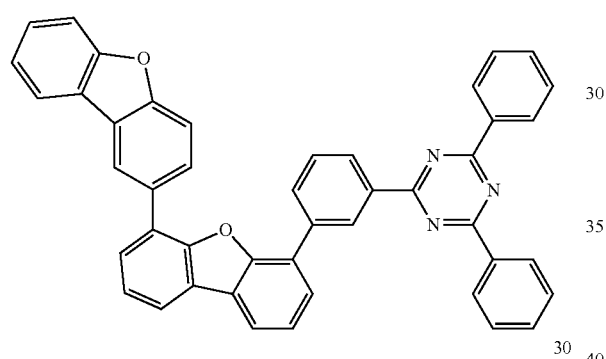
30
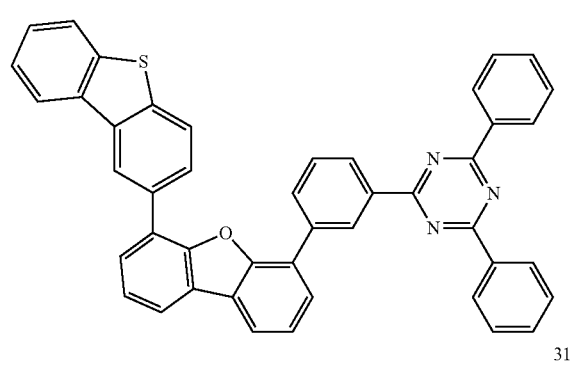
31
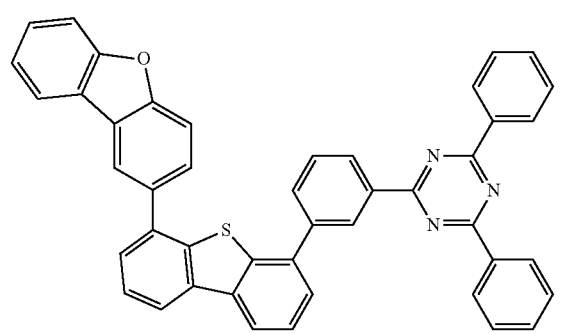
32
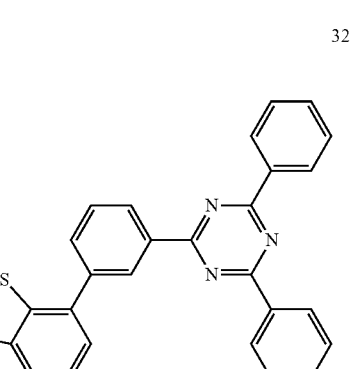
33
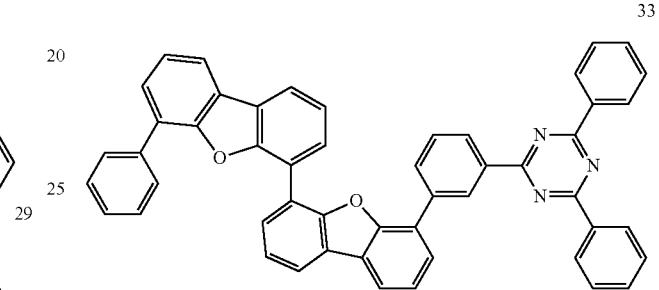
34
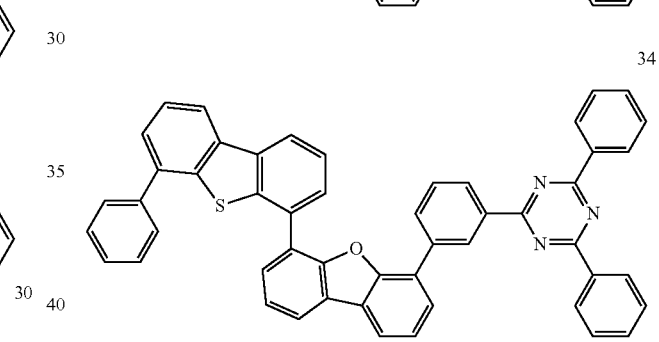
35
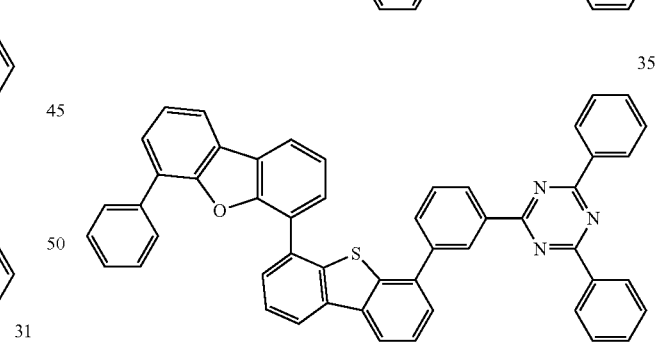
36
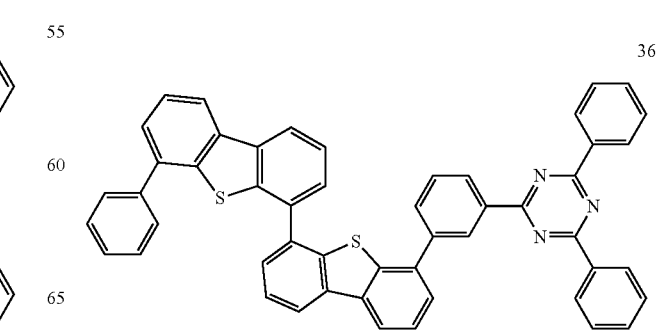

37
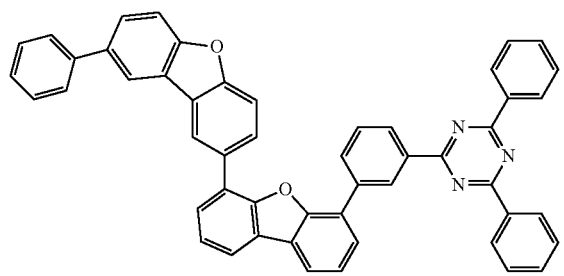
38
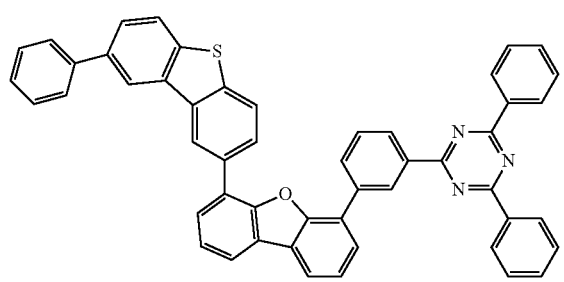
39
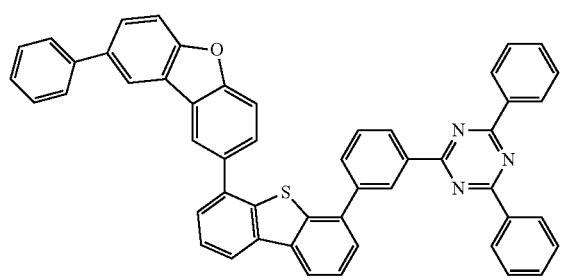
40
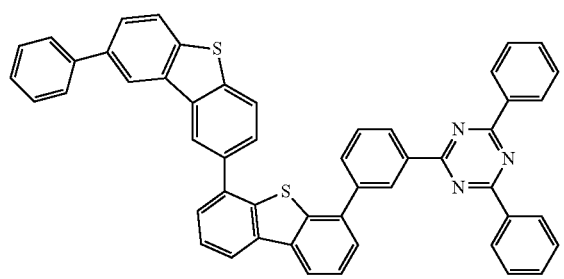
41
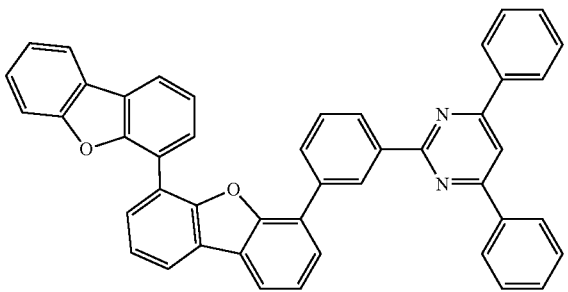
42
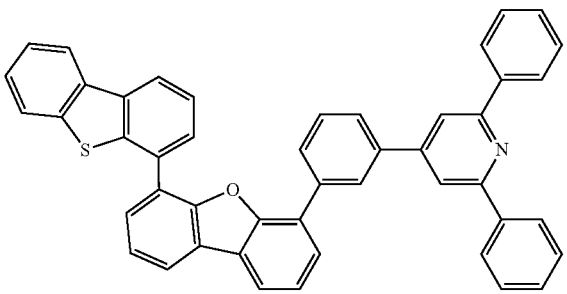
43
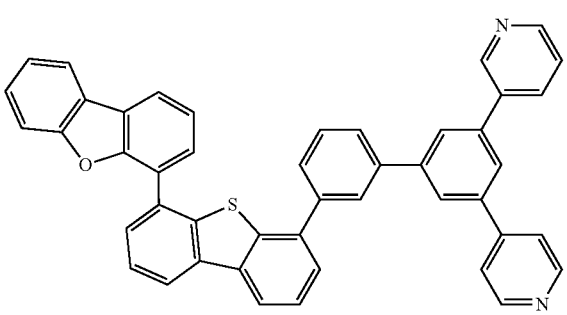
44
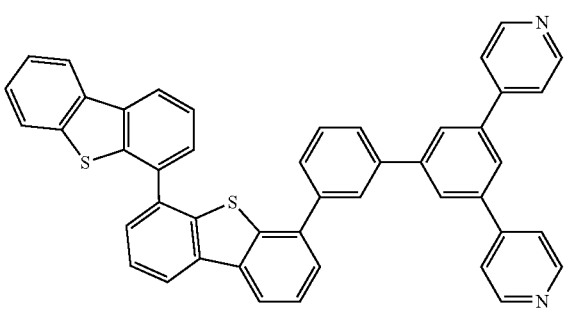
45
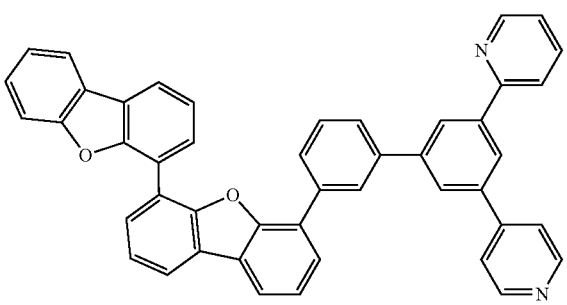
46
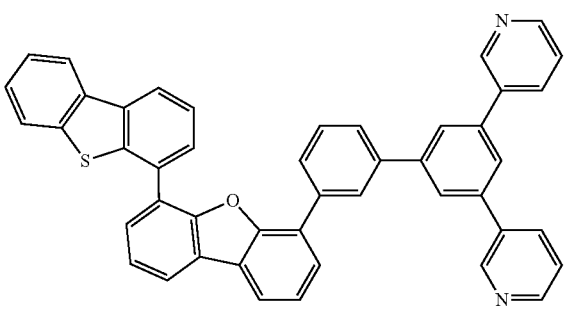

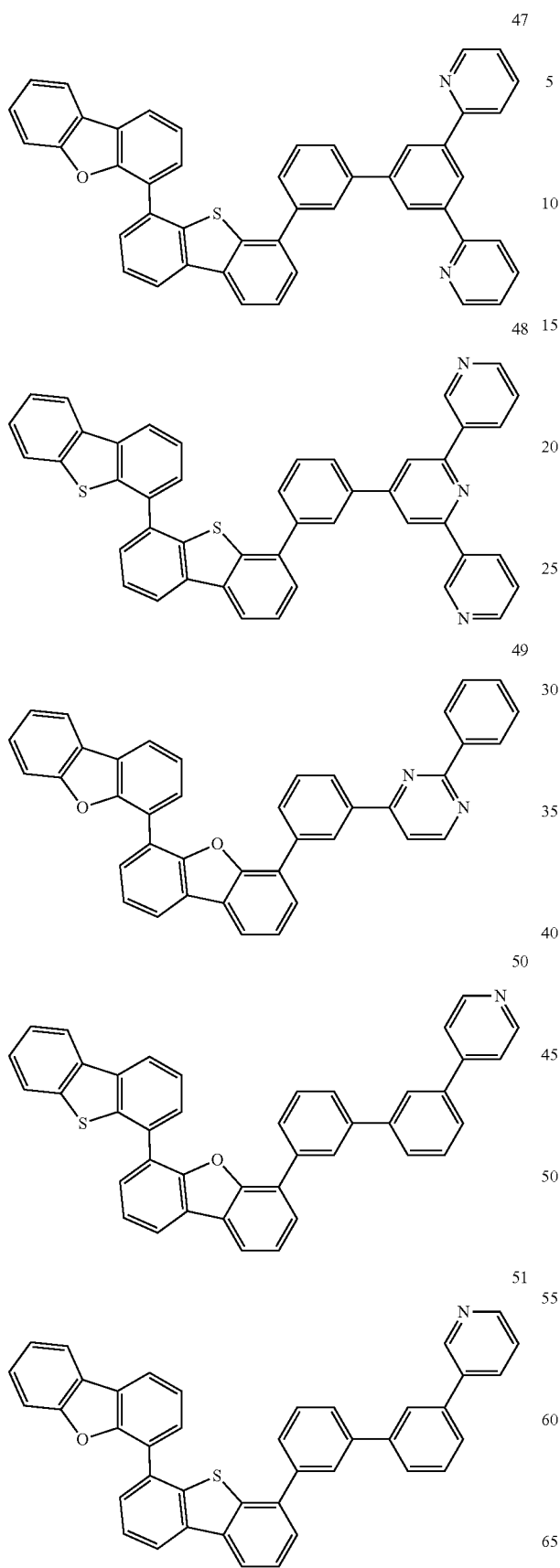
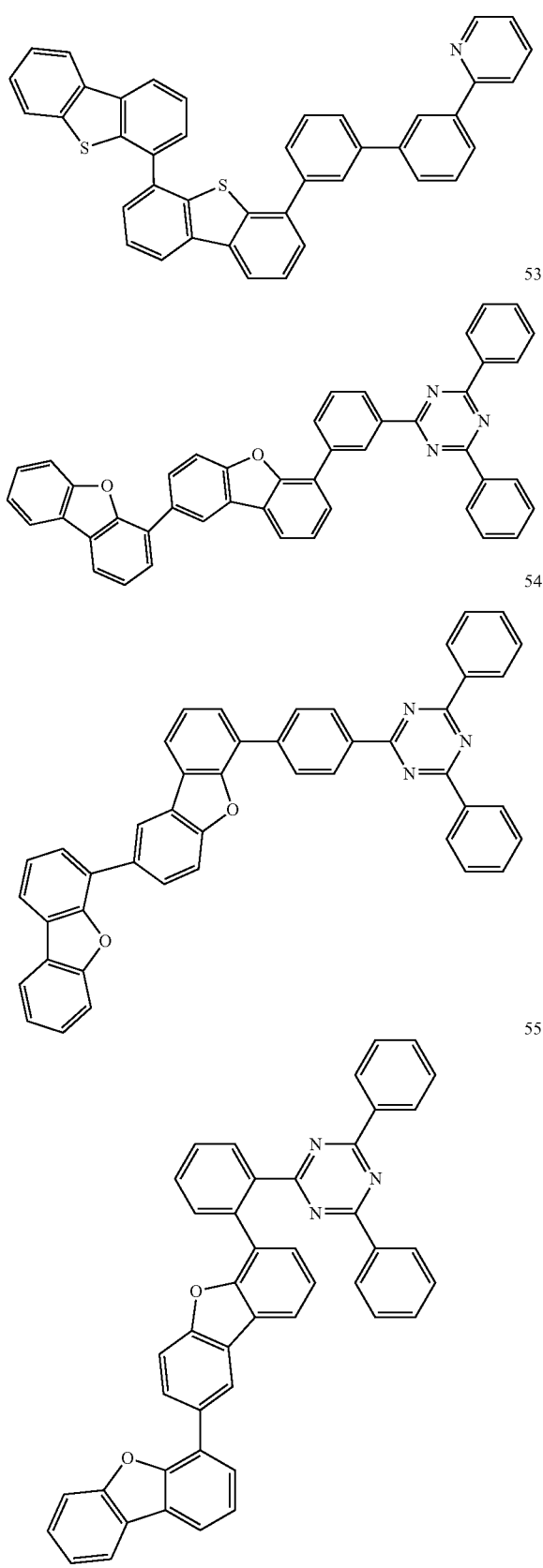

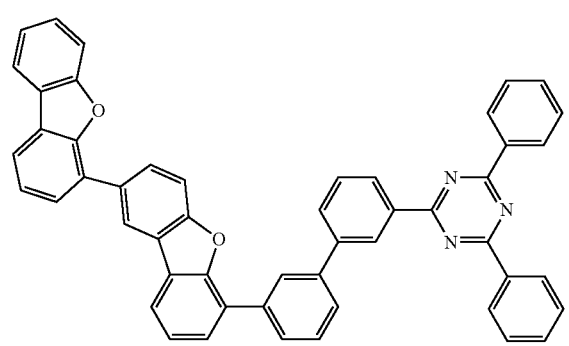
56
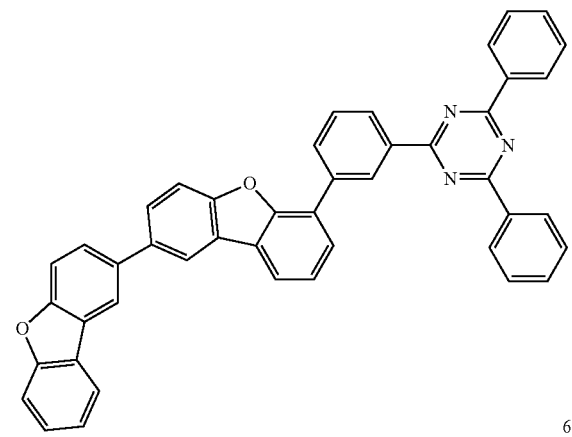
59
57
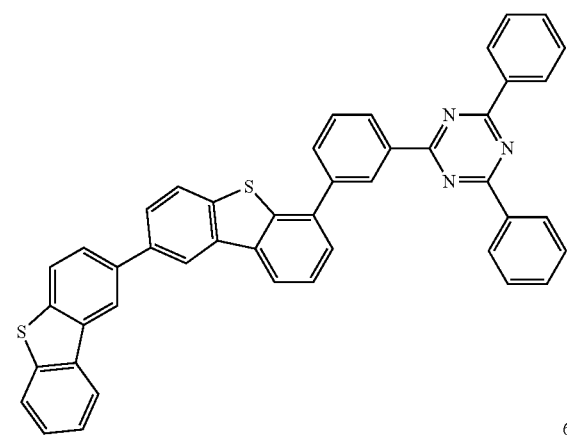
60
58
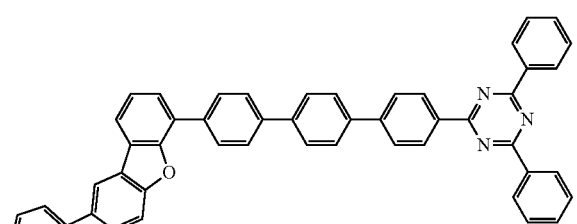
61
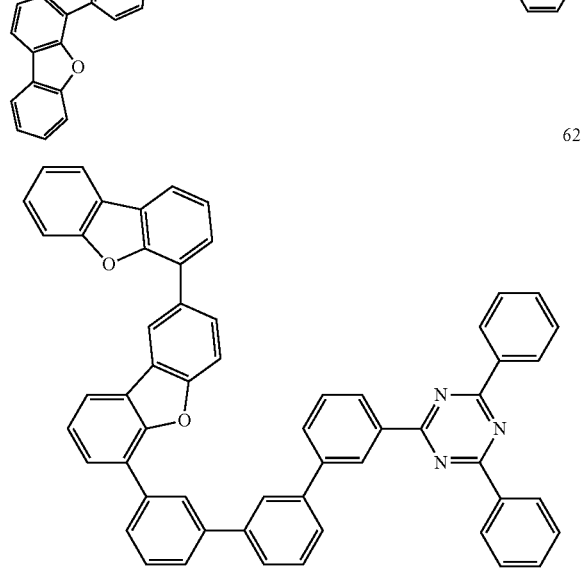
62

-continued

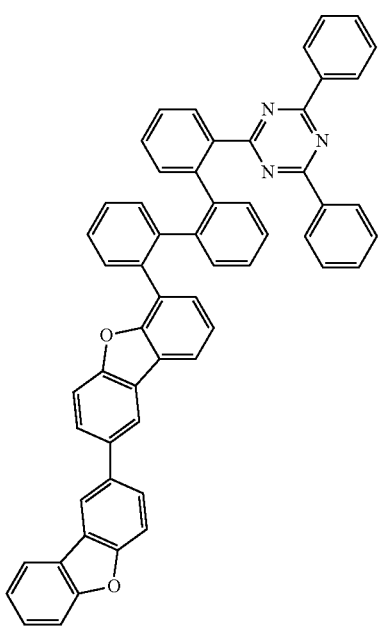

63

Hereinafter, an organic optoelectronic device including the organic compound is described.

The organic optoelectronic device may be any device to convert electrical energy into photoenergy and vice versa without particular limitation, and may be, for example an organic photoelectric device, an organic light emitting diode, an organic solar cell, and an organic photo-conductor drum.

Herein, an organic light emitting diode as one example of an organic optoelectronic device is described.

FIGS. 1 and 2 are cross-sectional views of an organic light emitting diode according to one embodiment.

Referring to FIG. 1, an organic optoelectronic diode 100 according to one embodiment includes an anode 120 and a cathode 110 facing each other and an organic layer 105 interposed between the anode 120 and the cathode 110.

The anode 120 may be made of a conductor having a large work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes an emission layer 130 including the organic compound.

The emission layer 130 may include, for example the organic compound alone, a mixture of at least two kinds of the organic compound, or a mixture of the organic compound and other compound. When the organic compound is mixed with the other compound, for example they may be included as a host and a dopant, wherein the organic compound may be, for example included as a host. The host may be, for example a phosphorescent host or a fluorescent host, for example a phosphorescent host.

When the organic compound is included as a host, the dopant may be an inorganic, organic, or organic/inorganic compound, and one or two dopants may be included.

Examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$L_2MX$ [Chemical Formula Z]

In Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidendate ligand.

Referring to FIG. 2, an organic light emitting diode 200 further includes a hole auxiliary layer 140 as well as an emission layer 130. The hole auxiliary layer 140 may further increase hole injection and/or hole mobility between the anode 120 and emission layer 130 and block electrons. The hole auxiliary layer 140 may be, for example a hole transport layer (HTL), a hole injection layer (HIL), and/or an electron blocking layer, and may include at least one layer. The organic compound may be included in the emission layer 130 and/or the hole auxiliary layer 140.

In one embodiment of the present invention, in FIG. 1 or 2, the organic layer 105 of the organic light emitting diode may further include an electron transport layer (ETL), an electron injection layer (EIL), a hole injection layer (HIL), and the like.

The organic light emitting diodes 100 and 200 may be manufactured by forming an anode or a cathode on a substrate, forming an organic layer in accordance with a dry coating method such as evaporation, sputtering, plasma plating, and ion plating; or a wet coating method such as spin coating, slit coating, dipping, flow coating and inkjet printing; and forming a cathode or an anode thereon.

The organic light emitting diode may be applied to an organic light emitting display device.

MODE FOR INVENTION

Hereinafter, the embodiments are illustrated in more detail with reference to examples. These examples, however, are not in any sense to be interpreted as limiting the scope of the invention.

Synthesis of Intermediate

Synthesis Example 1: Synthesis of Intermediate I-1

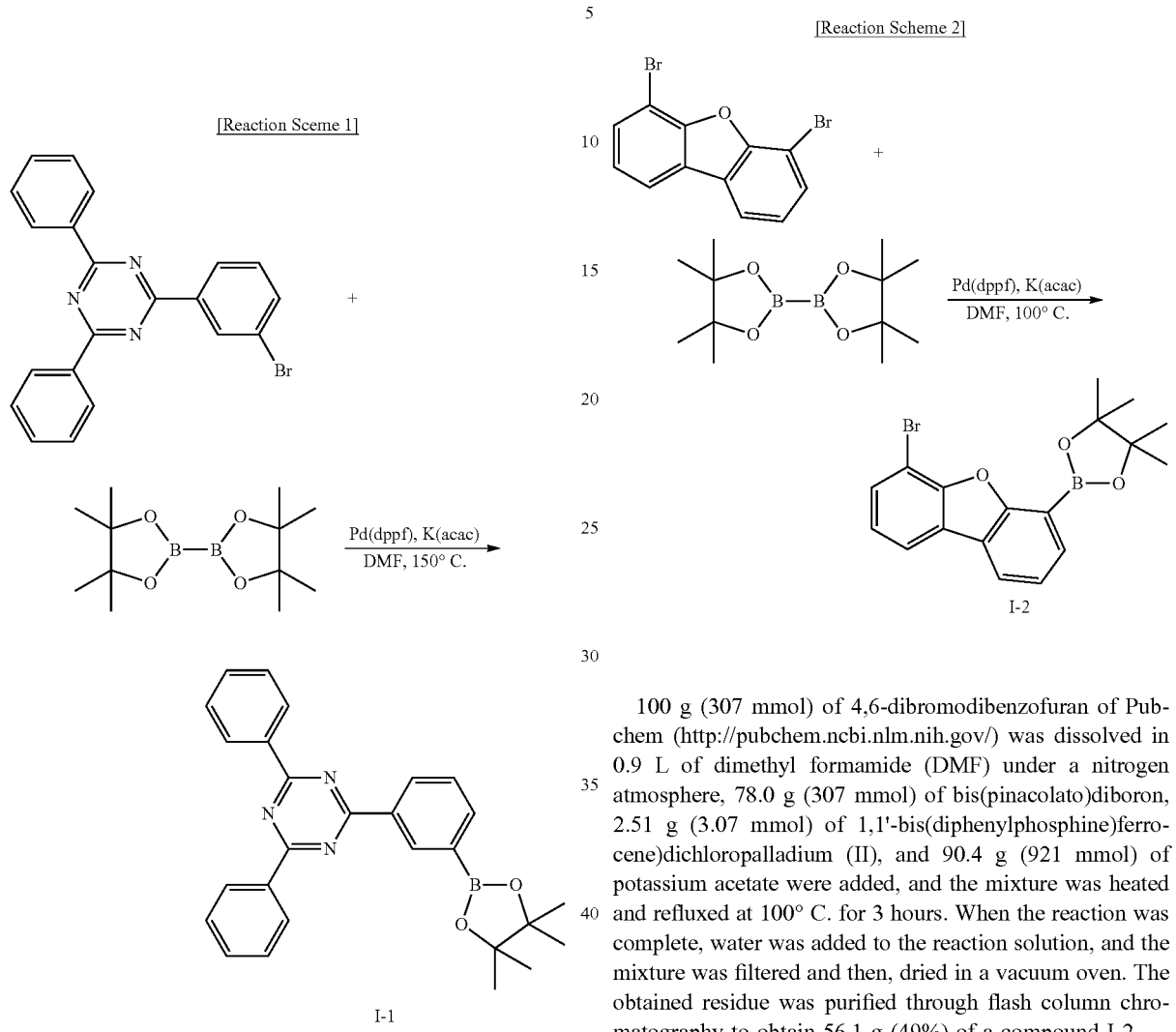

100 g (258 mmol) of 2-(3-bromophenyl)-4,6-diphenyl-1,3,5-triazine of Shenzhen gre-syn chemical technology (http://www.gre-syn.com/) was dissolved in 0.9 L of dimethyl formamide (DMF) under a nitrogen atmosphere, and 78.5 g (309 mmol) of bis(pinacolato)diboron and 2.10 g (2.58 mmol) of 1,1'-bis(diphenylphosphine)ferrocene)dichloropalladium (II), and 75.8 g (773 mmol) of potassium acetate were added, and the mixture was heated and refluxed at 150° C. for 3 hours. When the reaction was complete, water was added to the reaction solution, and the mixture was filtered and then, dried in a vacuum oven. The obtained residue was purified through flash column chromatography to obtain 79.7 g (71%) of a compound I-1.

HRMS (70 eV, EI+): m/z calcd for $C_{27}H_{26}BN_3O_2$: 435.2118. found: 435.

Elemental Analysis: C, 74%; H, 6%

Synthesis Example 2: Synthesis of Intermediate I-2

100 g (307 mmol) of 4,6-dibromodibenzofuran of Pubchem (http://pubchem.ncbi.nlm.nih.gov/) was dissolved in 0.9 L of dimethyl formamide (DMF) under a nitrogen atmosphere, 78.0 g (307 mmol) of bis(pinacolato)diboron, 2.51 g (3.07 mmol) of 1,1'-bis(diphenylphosphine)ferrocene)dichloropalladium (II), and 90.4 g (921 mmol) of potassium acetate were added, and the mixture was heated and refluxed at 100° C. for 3 hours. When the reaction was complete, water was added to the reaction solution, and the mixture was filtered and then, dried in a vacuum oven. The obtained residue was purified through flash column chromatography to obtain 56.1 g (49%) of a compound I-2.

HRMS (70 eV, EI+): m/z calcd for $C_{18}H_{18}BBrO_3$: 372.0532. found: 372.

Elemental Analysis: C, 58%; H, 5%

Synthesis Example 3: Synthesis of Intermediate I-3

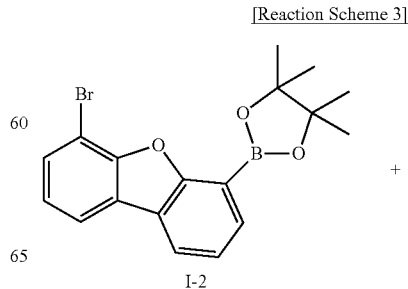

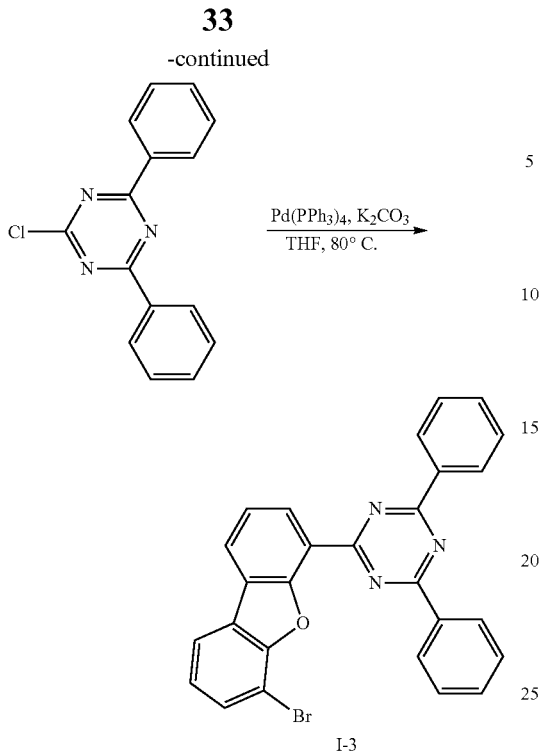

50 g (134 mmol) of the compound I-2 was dissolved in 0.5 L of tetrahydrofuran (THF) under a nitrogen atmosphere, 43.1 g (161 mmol) of 2-chloro-4,6-diphenyl-1,3,5-triazine, and 1.09 g (1.34 mmol) of tetrakis(triphenylphosphine) palladium were added thereto and then stirred. 32.9 g (335 mmol) of potassium carbonate saturated in water was added thereto, and the resulting mixture was heated and refluxed at 80° C. for 12 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was purified through flash column chromatography to obtain 25.6 g (40%) of a compound I-3.

HRMS (70 eV, EI+): m/z calcd for C27H16BrN3O: 478.3394. found: 478.

Elemental Analysis: C, 68%; H, 3%

Synthesis Example 4: Synthesis of Intermediate I-4

[Reaction Scheme 4]

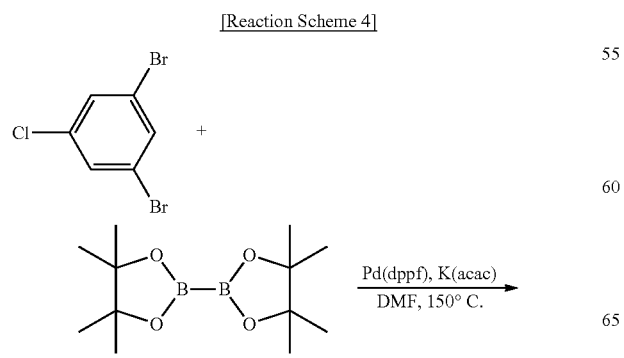

100 g (370 mmol) of 1,3-dibromo-5-chlorobenzene was dissolved in 1.7 L of dimethyl formamide (DMF) under a nitrogen atmosphere, 235 g (925 mmol) of bis(pinacolato) diboron, 6.04 g (7.40 mmol) of 1,1'-bis(diphenylphosphine) ferrocene)dichloropalladium (II), and 182 g (1,850 mmol) of potassium acetate were added, and the mixture was heated and refluxed at 150° C. for 5 hours. When the reaction was complete, water was added to the reaction solution, and the mixture was filtered and then, dried in a vacuum oven. The obtained residue was purified through flash column chromatography to obtain 87.7 g (65%) of a compound I-4.

HRMS (70 eV, EI+): m/z calcd for C18H27B2ClO4: 364.1784. found: 364.

Elemental Analysis: C, 59%; H, 7%

Synthesis Example 5: Synthesis of Intermediate I-5

[Reaction Scheme 5]

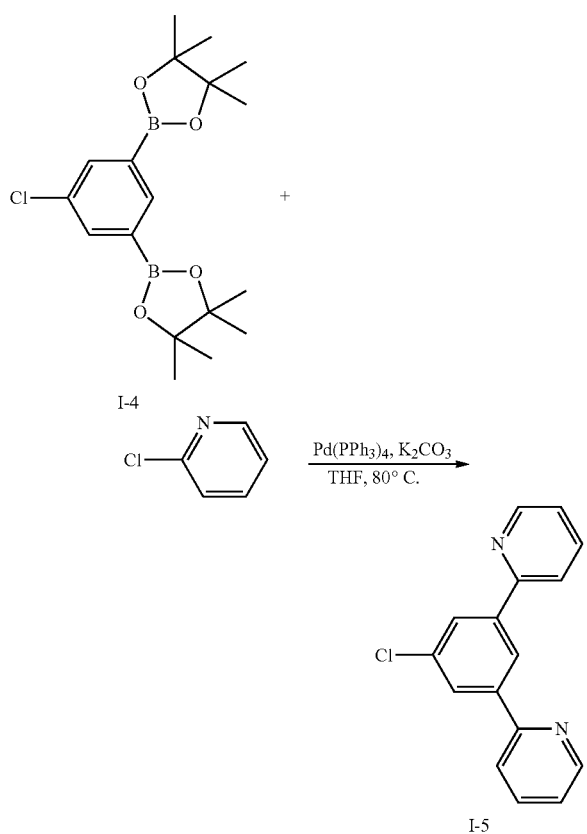

80 g (219 mmol) of the compound I-4 was dissolved in 0.7 L of tetrahydrofuran (THF) under a nitrogen atmosphere, and 52.3 g (461 mmol) of 2-chloropyridine and 2.53 g (2.19 mmol) of tetrakis(triphenylphosphine)palladium were added thereto and then stirred. 75.7 g (548 mmol) of potassium carbonate saturated in water was added thereto, and the resulting mixture was heated and refluxed at 80° C. for 6 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was purified through flash column chromatography to obtain 47.3 g (81%) of a compound I-5.

HRMS (70 eV, EI+): m/z calcd for O16H11ClN2: 266.7249. found: 267.

Elemental Analysis: C, 72%; H, 4%

Synthesis Example 6: Synthesis of Intermediate I-6

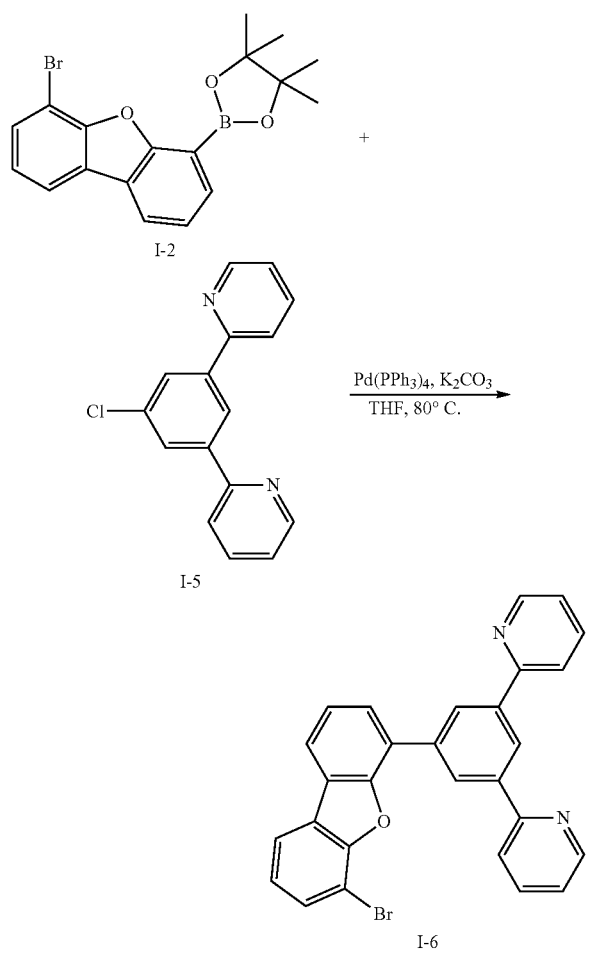

50 g (134 mmol) of the compound I-2 was dissolved in 0.5 L of tetrahydrofuran (THF) under a nitrogen atmosphere, 42.9 g (161 mmol) of 2-chloro-4,6-diphenyl-1,3,5-triazine, and 1.09 g (1.34 mmol) of tetrakis(triphenylphosphine) palladium were added thereto and then stirred. 32.9 g (335 mmol) of potassium carbonate saturated in water was added thereto, and the resulting mixture was heated and refluxed at 80° C. for 16 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was purified through flash column chromatography to obtain 27.5 g (43%) of a compound I-6.

HRMS (70 eV, EI+): m/z calcd for C28H17BrN2O: 476.0524. found: 476.

Elemental Analysis: C, 70%; H, 4%

Synthesis Example 7: Synthesis of Intermediate I-7

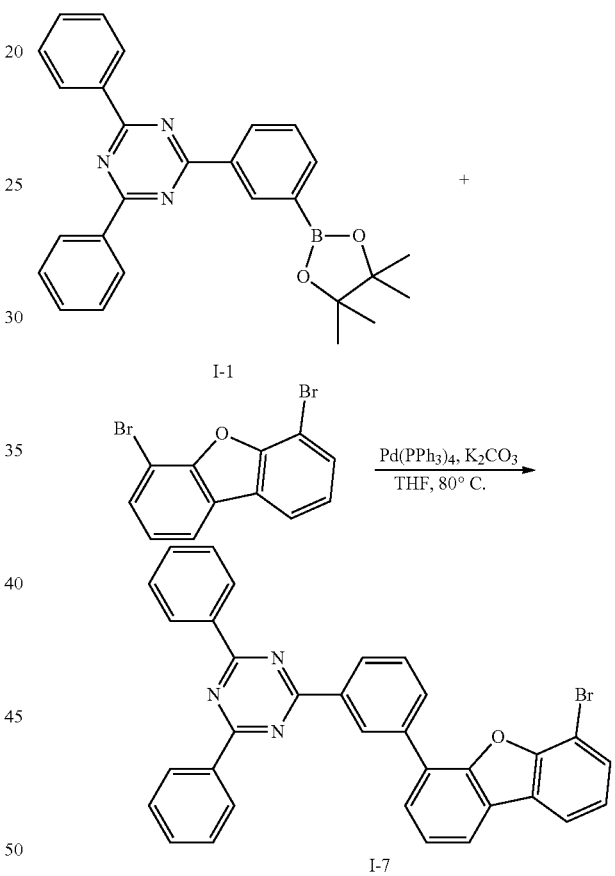

75 g (172 mmol) of the compound I-1 was dissolved in 0.7 L of tetrahydrofuran (THF) under a nitrogen atmosphere, and 56.1 g (172 mmol) of 4,6-dibromodibenzofuran of Pubchem (http://pubchem.ncbi.nlm.nih.gov/), and 1.99 g (1.72 mmol) of tetrakis(triphenylphosphine)palladium were added thereto and then stirred. 59.4 g (430 mmol) of potassium carbonate saturated in water was added thereto, and the resulting mixture was heated and refluxed at 80° C. for 14 hours. When the reaction was complete, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was purified through flash column chromatography to obtain 71.5 g (75%) of a compound I-7.

HRMS (70 eV, EI+): m/z calcd for C33H2OBrN3O: 553.0790. found: 553.
Elemental Analysis: C, 71%; H, 4%

Synthesis of Final Compound

Synthesis Example 8: Synthesis of Compound 1

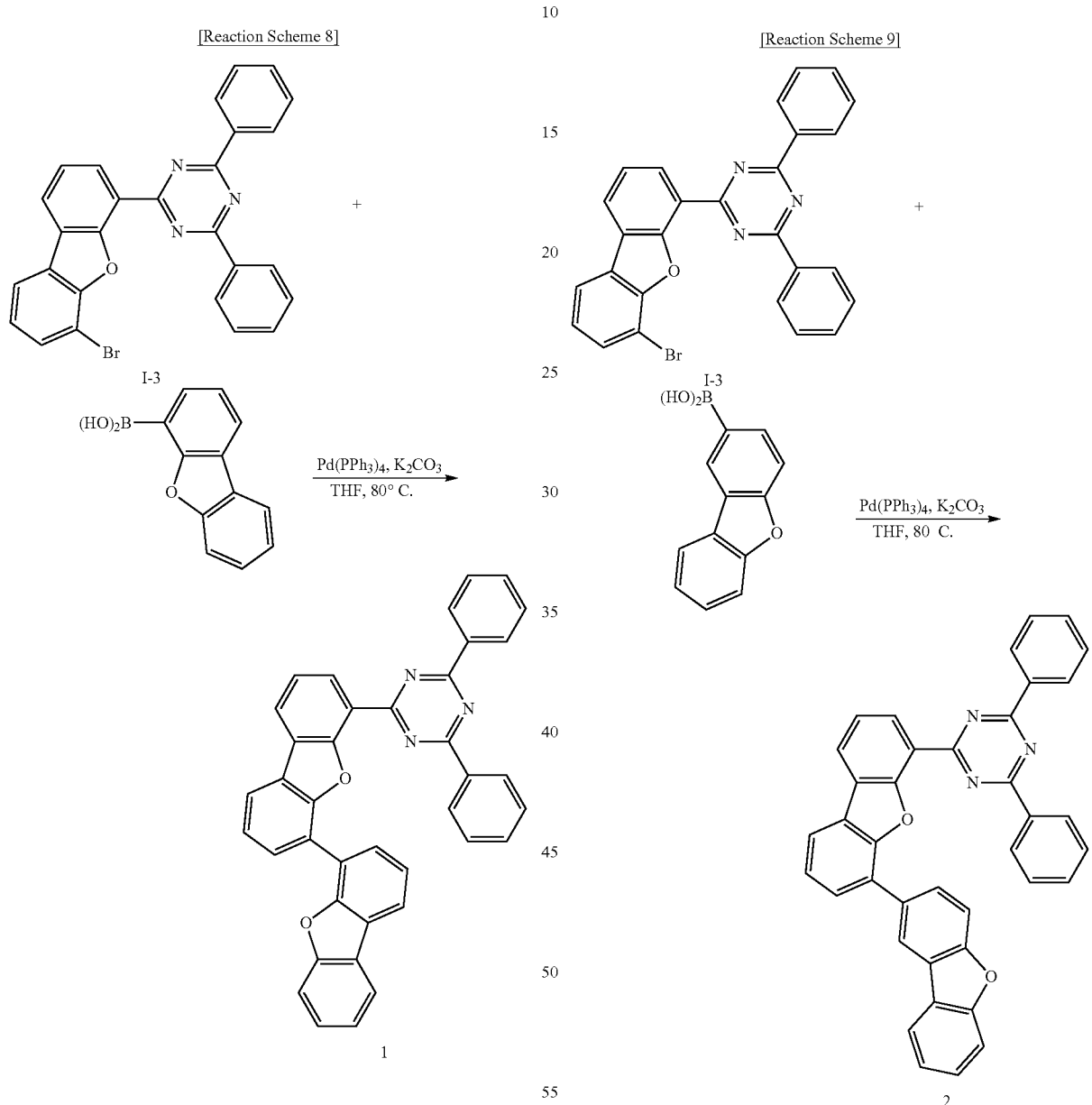

20 g (41.8 mmol) of the compound I-3 was dissolved in 0.15 L of tetrahydrofuran (THF) under a nitrogen atmosphere, and 9.75 g (46.0 mmol) of dibenzofuran-4-ylboronic acid and 0.49 g (0.42 mmol) of tetrakis(triphenylphosphine)palladium were added thereto and then stirred. 14.4 g (105 mmol) of potassium carbonate saturated in water was added thereto, and the resulting mixture was heated and refluxed at 80° C. for 7 hours. When the reaction was complete, water was added to the reaction solution, the mixture was extracted with dichloromethane (DCM), and the extract was treated with anhydrous MgSO4 to remove moisture therefrom, filtered, and concentrated under a reduced pressure. The obtained residue was purified through flash column chromatography to obtain 21.8 g (92%) of a compound 1.

HRMS (70 eV, EI+): m/z calcd for C39H23N3O2: 565.1790. found: 565.
Elemental Analysis: C, 83%; H, 4%

Synthesis Example 9: Synthesis of Compound 2

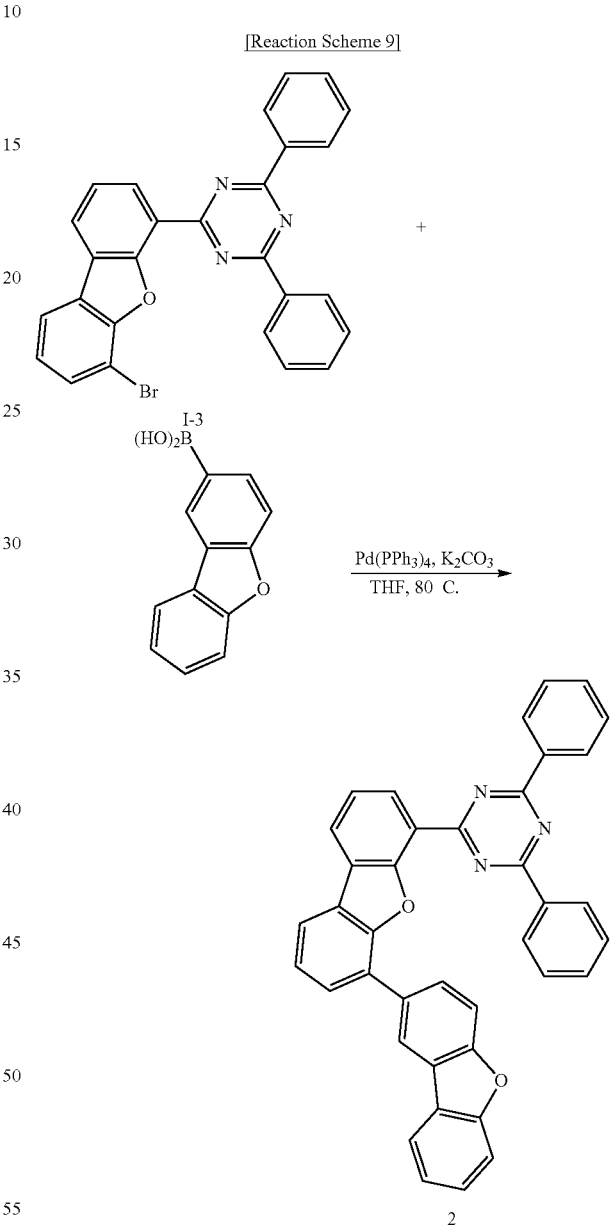

20 g (41.8 mmol) of the compound I-3 was dissolved in 0.15 L of tetrahydrofuran (THF) under a nitrogen atmosphere, and 9.75 g (46.0 mmol) of dibenzofuran-4-yl boronic acid and 0.49 g (0.42 mmol) of tetrakis(triphenylphosphine)palladium were added thereto and then stirred. 14.4 g (105 mmol) of potassium carbonate saturated in water was added thereto, and the resulting mixture was heated and refluxed at 80° C. for 7 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was purified through flash column chromatography to obtain 20.8 g (88%) of a compound 2.

HRMS (70 eV, EI+): m/z calcd for C39H23N3O2: 565.1790. found: 565.

Elemental Analysis: C, 83%; H, 4%

Synthesis Example 10: Synthesis of Compound 21

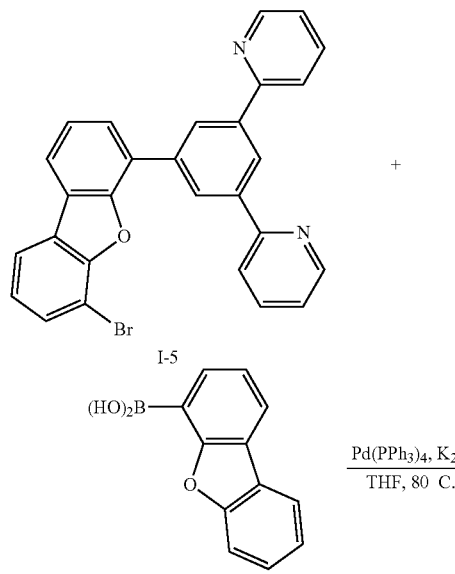

20 g (41.9 mmol) of the compound 1-6 was dissolved in 0.15 L of tetrahydrofuran (THF) under a nitrogen atmosphere, and 9.77 g (46.1 mmol) of dibenzofuran-4-yl boronic acid and 0.42 g (0.48 mmol) of tetrakis(triphenylphosphine)palladium were added thereto and then stirred. 14.5 g (105 mmol) of potassium carbonate saturated in water was added thereto, and the resulting mixture was heated and refluxed at 80° C. for 8 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was purified through flash column chromatography to obtain 20.8 g (88%) of a compound 21.

HRMS (70 eV, EI+): m/z calcd for C40H24N2O2: 564.1838. found: 564.

Elemental Analysis: C, 85%; H, 4%

Synthesis Example 11: Synthesis of Compound 25

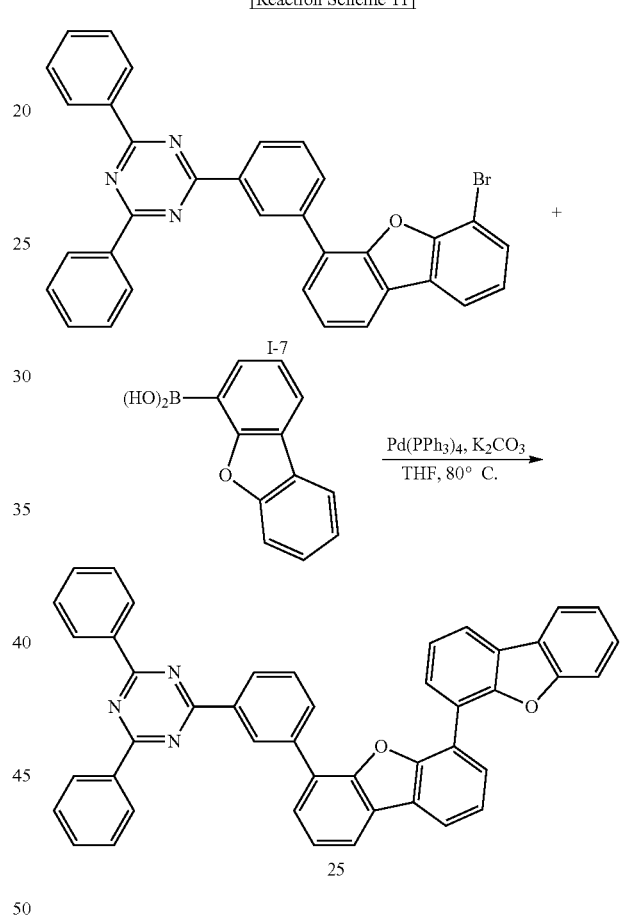

20 g (36.1 mmol) of the compound I-7 was dissolved in 0.15 L of tetrahydrofuran (THF) under a nitrogen atmosphere, 8.41 g (39.7 mmol) of dibenzofuran-4-yl boronic acid and 0.42 g (0.36 mmol) of tetrakis(triphenylphosphine) palladium were added thereto and then stirred. 12.5 g (90.3 mmol) of potassium carbonate saturated in water was added thereto, and the resulting mixture was heated and refluxed at 80° C. for 10 hours. When the reaction was complete, water was added to the reaction solution, the mixture was extracted with dichloromethane (DCM), and the extract was treated with anhydrous MgSO₄ to remove moisture therefrom, filtered, and concentrated under a reduced pressure. The obtained residue was purified through flash column chromatography to obtain 18.5 g (80%) of a compound 25.

HRMS (70 eV, EI+): m/z calcd for C45H27N3O2: 641.2103. found: 641.

Elemental Analysis: C, 84%; H, 4%

Synthesis Example 12: Synthesis of Compound 29

[Reaction Scheme 12]

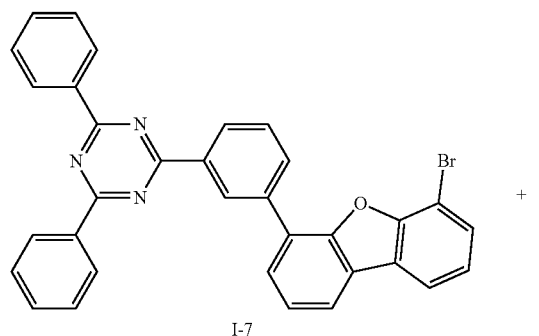

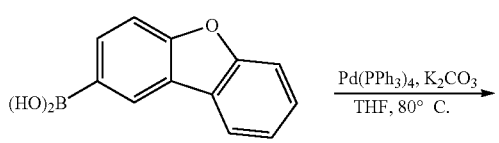

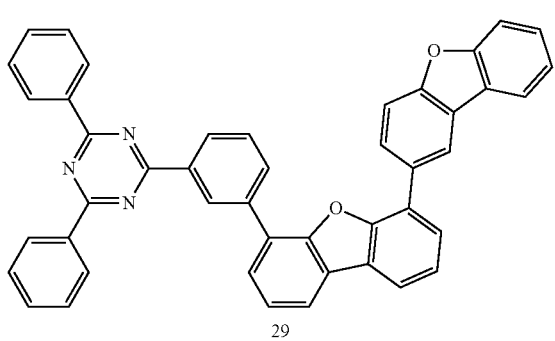

20 g (36.1 mmol) of the compound I-7 was dissolved in 0.15 L of tetrahydrofuran (THF) under a nitrogen atmosphere, and 8.41 g (39.7 mmol) of dibenzofuran-4-yl boronic acid and 0.42 g (0.36 mmol) of tetrakis(triphenylphosphine)palladium were added thereto and then stirred. 12.5 g (90.3 mmol) of potassium carbonate saturated in water was added thereto, and the resulting mixture was heated and refluxed at 80° C. for 11 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was purified through flash column chromatography to obtain 17.6 g (76%) of a compound 29.

HRMS (70 eV, EI+): m/z calcd for C45H27N3O2: 641.2103. found: 641.

Elemental Analysis: C, 84%; H, 4%

Synthesis Example 13: Synthesis of HOST 1 as Comparative Example

[Reaction Scheme 13]

20 g (45.9 mmol) of the compound I-1 was dissolved in 0.2 L of tetrahydrofuran (THF) under a nitrogen atmosphere, and 11.4 g (45.9 mmol) of 4-bromodibenzofuran and 0.53 g (0.46 mmol) of tetrakis(triphenylphosphine)palladium were added thereto and then stirred. 15.9 g (115 mmol) of potassium carbonate saturated in water was added thereto, and the resulting mixture was heated and refluxed at 80° C. for 8 hours. When the reaction was complete, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was purified through flash column chromatography to obtain 19.6 g (90%) of a compound HOST1.

HRMS (70 eV, EI+): m/z calcd for C33H21N3O: 475.1685. found: 475.

Elemental Analysis: C, 83%; H, 4%

Manufacture of Organic Light Emitting Diode

Example 1

The compound 1 obtained in Synthesis Example 8 was used as a host of an emission layer and Ir(PPy)$_3$ was used as a dopant of an emission layer to manufacture an organic light emitting diode.

A 1000 Å-thick ITO was used as an anode, and a 1000 Å-thick aluminum (Al) as a cathode. Specifically, the organic light emitting diode was manufactured in a method of cutting an ITO glass substrate having sheet resistance of 15 Ω/cm² into a size of 50 mm×50 mm×0.7 mm, ultrasonic wave-cleaning it in acetone, isopropylalcohol, and pure water respectively for 15 minutes and UV ozone-cleaning it for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of 650×10⁻⁷ Pa at a deposition rate of 0.1 to 0.3 nm/s. Subsequently, a 300 Å-thick film as an emission layer was formed by using the compound 8 according to Synthesis Example 1 under the same vacuum deposition condition as above, and herein, Ir(PPy)₃ as a phosphorescent dopant was simultaneously deposited. Herein, the phosphorescent dopant was deposited in an amount of 7 wt % based on 100 wt % of the total amount of the emission layer by adjusting a deposition rate.

On the emission layer, a 50 Å-thick film as a hole blocking layer was formed by depositing bis(2-methyl-8-quinolinolate)-4-(phenylphenolato)aluminum (BAlq) under the same vacuum deposition condition as above. Subsequently, a 200 Å-thick film as an electron transport layer was formed by depositing Alq3 under the same vacuum deposition condition as above. On the electron transport layer, LiF and Al were sequentially deposited as a cathode, manufacturing the organic light emitting diode.

The organic light emitting diode had a structure of ITO/NPB (80 nm)/EML (compound 1 (93 wt %)+Ir(PPy)₃ (7 wt %), 30 nm)/Balq (5 nm)/Alq₃ (20 nm)/LiF (1 nm)/Al (100 nm).

Example 2

An organic light emitting diode was manufactured according to the same method as Example 1 except that the compound 2 of Synthesis Example 9 was used instead of the compound 1 of Synthesis Example 8.

Example 3

An organic light emitting diode was manufactured according to the same method as Example 1 except that the compound 21 of Synthesis Example 10 was used instead of the compound 1 of Synthesis Example 8.

Example 4

An organic light emitting diode was manufactured according to the same method as Example 1 except that the compound 25 of Synthesis Example 11 was used instead of the compound 1 of Synthesis Example 8.

Example 5

An organic light emitting diode was manufactured according to the same method as Example 1 except that the compound 29 of Synthesis Example 12 was used instead of the compound 1 of Synthesis Example 8.

Comparative Example 1

An organic light emitting diode was manufactured according to the same method as Example 1 except that CBP having the following the structure was used instead of the compound 1 of Synthesis Example 8.

Comparative Example 2

An organic light emitting diode was manufactured according to the same method as Example 1 except that HOST1 of Synthesis Example 13 was used instead of the compound 1 of Synthesis Example 8.

Comparative Example 3

An organic light emitting diode was manufactured according to the same method as Example 1 except that HOST2 of Synthesis Example 13 was used instead of the compound 1 of Synthesis Example 8. The HOST2 was synthesized according to the same method as disclosed in WO 2013-077352 A1.

The structures of NPB, BAlq, CBP, Ir(PPy)₃, and HOST2 used to manufacture the organic light emitting diodes are as follows.

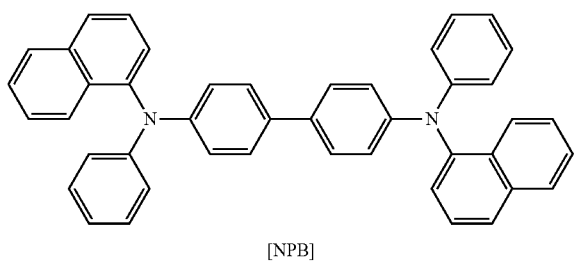

[NPB]

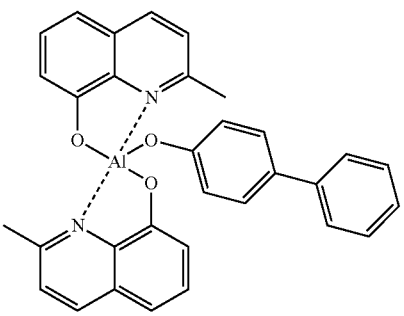

[BAlq]

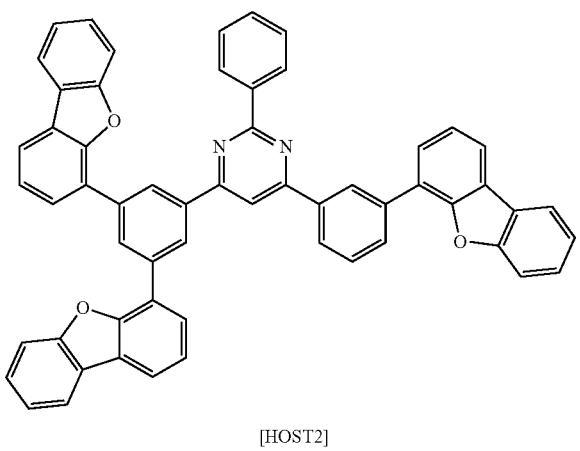

[HOST2]

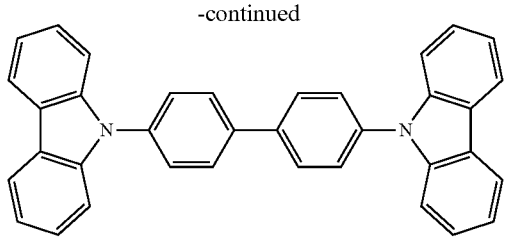

[CBP]

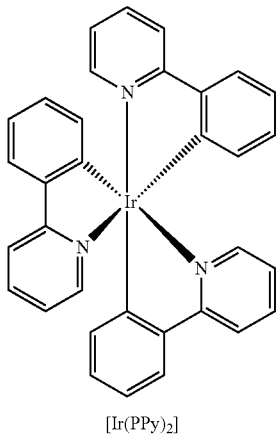

[Ir(PPy)₂]

Evaluation

Current density change, luminance change, and luminous efficiency of each organic light emitting diode according to Examples 1 to 5 and Comparative Examples 1 to 3 were measured.

Specific measurement methods are as follows, and the results are shown in the following Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm²) were calculated by using the luminance, current density, and voltages (V) from the items (1) and (2).

(4) Measurement of Life-Span

A life span was obtained by measuring a time when current efficiency (cd/A) was decreased down to 90%, while luminance (cd/m²) was maintained to be 5000 cd/m².

TABLE 1

| Nos. | Host of Emission layer | Driving voltage (V) | Color (EL color) | Efficiency (cd/A) | 90% life-span (h)@ 5000 cd/m² |
|---|---|---|---|---|---|
| Example 1 | compound 1 | 4.0 | Green | 84.2 | 630 |
| Example 2 | compound 2 | 3.8 | Green | 86.7 | 560 |
| Example 3 | compound 21 | 4.5 | Green | 62.2 | 500 |
| Example 4 | compound 25 | 4.1 | Green | 78.1 | 1,110 |
| Example 5 | compound 29 | 3.9 | Green | 80.6 | 1,000 |
| Comparative Example 1 | CBP | 4.8 | Green | 31.4 | 40 |
| Comparative Example 2 | HOST1 | 4.8 | Green | 42.1 | 280 |
| Comparative Example 3 | HOST2 | 4.1 | Green | 75.3 | 190 |

Referring to Table 1, the organic light emitting diodes of Examples 1 to 5 exhibited remarkably improved luminous efficiency and life-span compared with the organic light emitting diodes according to Comparative Examples 1 to Comparative Example 2.

Specifically, a light emitting material used for the organic light emitting diodes of Examples 1 to 5 had a bipolar structure unlike a light emitting material used for the organic light emitting diode of Comparative Example 1 and thus showed a satisfactory balance between electrons and holes and resultantly high efficiency and a low driving voltage. In addition, the bipolar structure turned out to easily form excitons as well as smoothen a flow of the electrons and holes and thus prevent overloading an emission layer and resultantly, improve the life-span of the organic light emitting diodes.

Comparing the organic light emitting diodes according to Examples 1 to 5 with the organic light emitting diode according to Comparative Example 2, the organic light emitting diodes used a compound including one more dibenzofuran group and thus had an effect of balancing the dibenzofuran group having weak hole characteristics and a triazine group having strong electron characteristics and thus lowering a driving voltage. In addition, the compound turned out to prevent overloading the emission layer and thus improve the life-span of the organic light emitting diodes according to Examples 1 to 5.

Comparing the organic light emitting diodes according to Examples 1 to 5 with the organic light emitting diode according to Comparative Example 2, the organic light emitting diodes according to Examples 1 to 5 had high efficiency due to localization of a functional group having hole characteristics and a group having electron characteristics, a low driving voltage, and high life-span characteristics, while the organic light emitting diode according to Comparative Example 3 showed insufficient life-span characteristics due to an interference effect between a functional group having hole characteristics and a group having electron characteristics due to no localization of the functional group having hole characteristics and the group having electron characteristics While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode
105: organic layer
110: cathode 120: anode
130: emission layer
140: hole auxiliary layer

The invention claimed is:

1. An organic compound represented by Chemical Formula 1:

[Chemical Formula 1]

wherein, in Chemical Formula 1, $X^1$ and $X^2$ are independently S, O, SO, or $SO_2$, provided that at least one of $X^1$ and $X^2$ is O, $L^1$ and $L^2$ are independently a single bond or a C6 to C20 substituted or unsubstituted arylene group, Z is independently N, C, or $CR^a$, provided that at least two of Z are N, $R^1$ and $R^2$ are independently hydrogen, deuterium, a substituted or unsubstituted C1 to C20 alkyl group, an unsubstituted C6 to C20 aryl group, or a combination thereof, $R^3$ to $R^{12}$ and $R^a$ are independently hydrogen, deuterium, unsubstituted C1 to C20 alkyl group, unsubstituted C6 to C20 aryl group, or a combination thereof, and n1 and n2 are independently 0 or 1.

2. The organic compound of claim 1, wherein the organic compound is represented by Chemical Formula 2:

[Chemical Formula 2]

wherein, in Chemical Formula 2, $X^1$ and $X^2$ are independently S, O, SO, or $SO_2$, provided that at least one of $X^1$ and $X^2$ is O, $L^1$ and $L^2$ are independently a single bond or a C6 to C20 substituted or unsubstituted arylene group, Z is independently N, C, or $CR^a$, provided that at least two of Z are N, $R^1$ and $R^2$ are independently hydrogen, deuterium, a substituted or unsubstituted C1 to C20 alkyl group, an unsubstituted C6 to C20 aryl group, or a combination thereof, $R^3$ to $R^{12}$ and $R^a$ are independently hydrogen, deuterium, a substituted or unsubstituted C1 to C20 alkyl group, a substituted or unsubstituted C6 to C20 aryl group, or a combination thereof, and n1 and n2 are independently 0 or 1.

3. The organic compound of claim 1, wherein the organic compound is represented by Chemical Formula 3 or 4:

[Chemical Formula 3]

[Chemical Formula 4]

wherein, in Chemical Formula 3 and 4, $X^1$ and $X^2$ are independently S, O, SO, or $SO_2$, provided that at least one of $X^1$ and $X^2$ is O, $L^1$ and $L^2$ are independently a single bond or a C6 to C20 substituted or unsubstituted arylene group, Z is independently N, C, or $CR^a$, provided that at least two of Z are N, $R^1$ and $R^2$ are independently hydrogen, deuterium, a substituted or unsubstituted C1 to C20 alkyl group, an unsubstituted C6 to C20 aryl group, or a combination thereof, $R^3$ to $R^{12}$ and $R^a$ are independently hydrogen, deuterium, a substituted or unsubstituted C1 to C20 alkyl group, a substituted or unsubstituted C6 to C20 aryl group, or a combination thereof, and n1 and n2 are independently 0 or 1.

4. The organic compound of claim 3, wherein the organic compound represented by Chemical Formula 3 is represented by Chemical Formula 3a or 3b:

[Chemical Formula 3a]

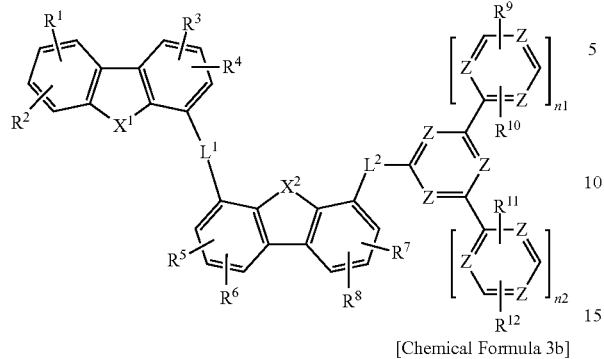

[Chemical Formula 3b]

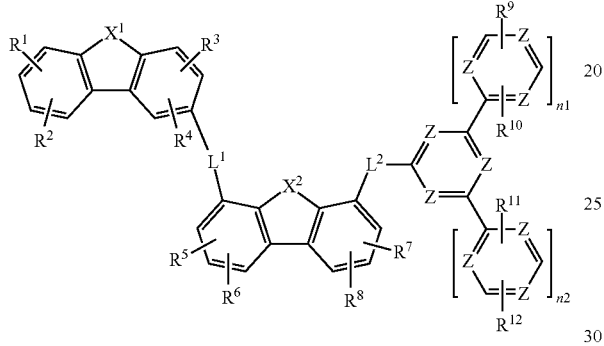

wherein, in Chemical Formula 3a and 3b,
$X^1$ and $X^2$ are independently S, O, SO, or $SO_2$, provided that at least one of $X^1$ and $X^2$ is O,
$L^1$ and $L^2$ are independently a single bond or a C6 to C20 substituted or unsubstituted arylene group,
Z is independently N, C, or $CR^a$, provided that at least two of Z are N,
$R^1$ and $R^2$ are independently hydrogen, deuterium, a substituted or unsubstituted C1 to C20 alkyl group, an unsubstituted C6 to C20 aryl group, or a combination thereof,
$R^3$ to $R^{12}$ and $R^a$ are independently hydrogen, deuterium, a substituted or unsubstituted C1 to C20 alkyl group, a substituted or unsubstituted C6 to C20 aryl group, or a combination thereof, and
n1 and n2 are independently 0 or 1.

5. The organic compound of claim 4, wherein:
the organic compound represented by Chemical Formula 3a is represented by Chemical Formula 3aa, and
the organic compound represented by Chemical Formula 3b is represented by Chemical Formula 3ba:

[Chemical Formula 3aa]

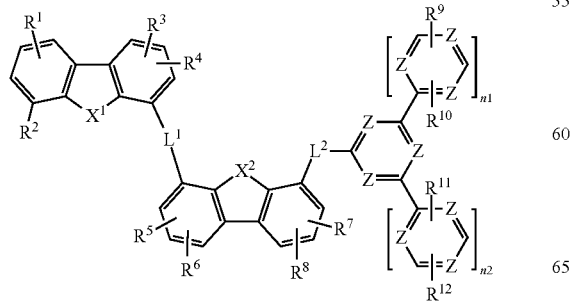

[Chemical Formula 3ba]

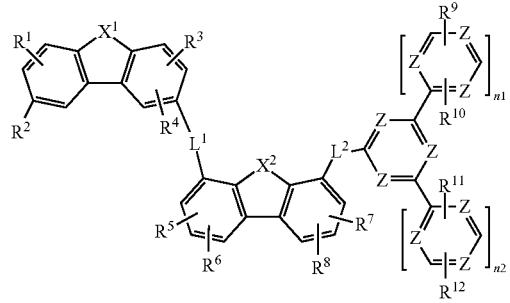

wherein, in Chemical Formula 3aa and 3ba,
$X^1$ and $X^2$ are independently S, O, SO, or $SO_2$, provided that at least one of $X^1$ and $X^2$ is O,
$L^1$ and $L^2$ are independently a single bond or a C6 to C20 substituted or unsubstituted arylene group,
Z is independently N, C, or $CR^a$, provided that at least two of Z are N,
$R^3$ to $R^{12}$, and $R^a$ are independently hydrogen, deuterium, a substituted or unsubstituted C1 to C20 alkyl group, a substituted or unsubstituted C6 to C20 aryl group, or a combination thereof,
$R^1$ and $R^2$ are independently hydrogen or an unsubstituted C6 to C20 aryl group, and
n1 and n2 are independently 0 or 1.

6. The organic compound of claim 3, wherein the organic compound represented by Chemical Formula 4 is represented by Chemical Formula 4a or 4b:

[Chemical Formula 4a]

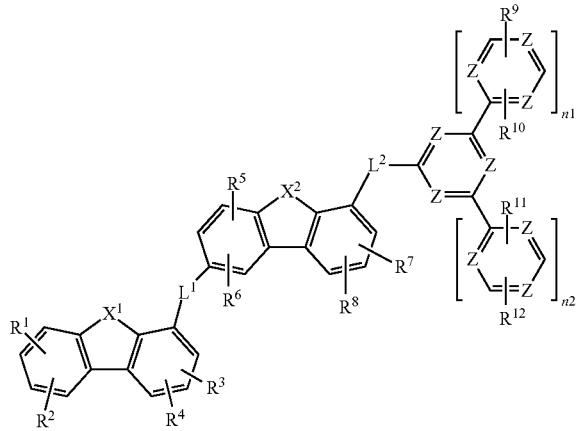

[Chemical Formula 4b]

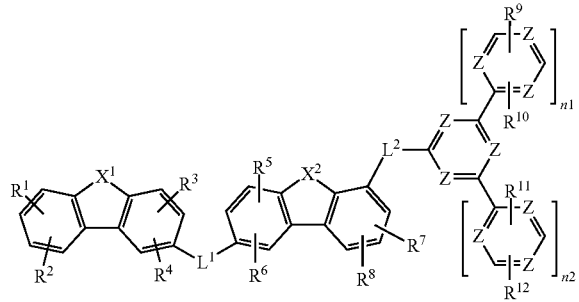

wherein, in Chemical Formulae 4a and 4b, $X^1$ and $X^2$ are independently S, O, SO, or $SO_2$, provided that at least one of $X^1$ and $X^2$ is O, $L^1$ and $L^2$ are independently a single bond or a C6 to C20 substituted or unsubstituted arylene group, Z is independently N, C, or $CR^a$, provided that at least two of Z are N, $R^1$ and $R^2$ are independently hydrogen, deuterium, a substituted or unsubstituted C1 to C20 alkyl group, an unsubstituted C6 to C20 aryl group, or a combination thereof, $R^3$ to $R^{12}$ and $R^a$ are independently hydrogen, deuterium, a substituted or unsubstituted C1 to C20 alkyl group, a substituted or unsubstituted C6 to C20 aryl group, or a combination thereof, and n1 and n2 are independently 0 or 1.

7. The organic compound of claim 6, wherein:
the organic compound represented by Chemical Formula 4a is represented by Chemical Formula 4aa, and
the organic compound represented by Chemical Formula 4b is represented by Chemical Formula 4ba:

[Chemical Formula 4aa]

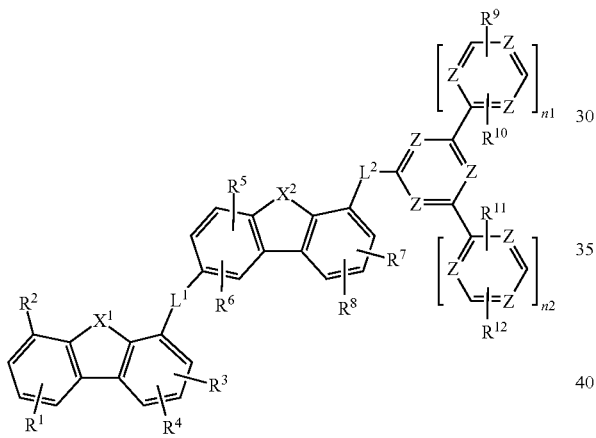

[Chemical Formula 4ba]

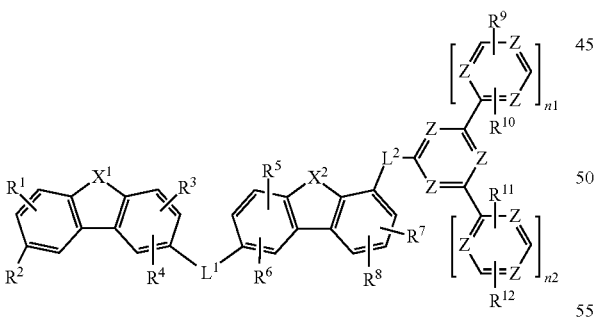

wherein, in Chemical Formulae 4aa and 4ba, $X^1$ and $X^2$ are independently S, O, SO, or $SO_2$, provided that at least one of $X^1$ and $X^2$ is O, $L^1$ and $L^2$ are independently a single bond or a C6 to C20 substituted or unsubstituted arylene group, Z is independently N, C, or $CR^a$, provided that at least two of Z are N, $R^3$ to $R^{12}$, and $R^a$ are independently hydrogen, deuterium, a substituted or unsubstituted C1 to C20 alkyl group, a substituted or unsubstituted C6 to C20 aryl group, or a combination thereof, $R^1$ and $R^2$ are independently hydrogen or an unsubstituted C6 to C20 aryl group, and n1 and n2 are independently 0 or 1.

8. The organic compound of claim 1, wherein the $L^1$ and $L^2$ are independently a single bond, unsubstituted phenylene group having a kink structure, a substituted or unsubstituted biphenylene group having a kink structure, or a substituted or unsubstituted terphenylene group having a kink structure.

9. The organic compound of claim 8, wherein the $L^1$ and $L^2$ are independently a single bond or one selected from substituted or unsubstituted groups of Group 1:

[Group 1]

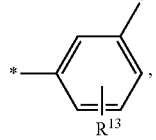

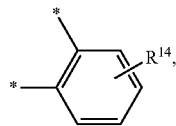

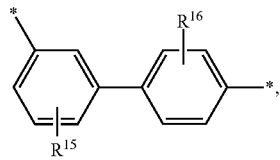

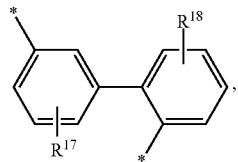

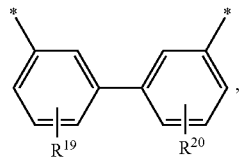

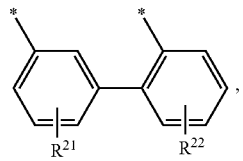

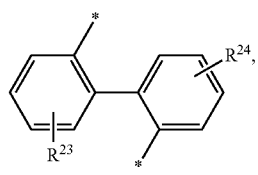

-continued

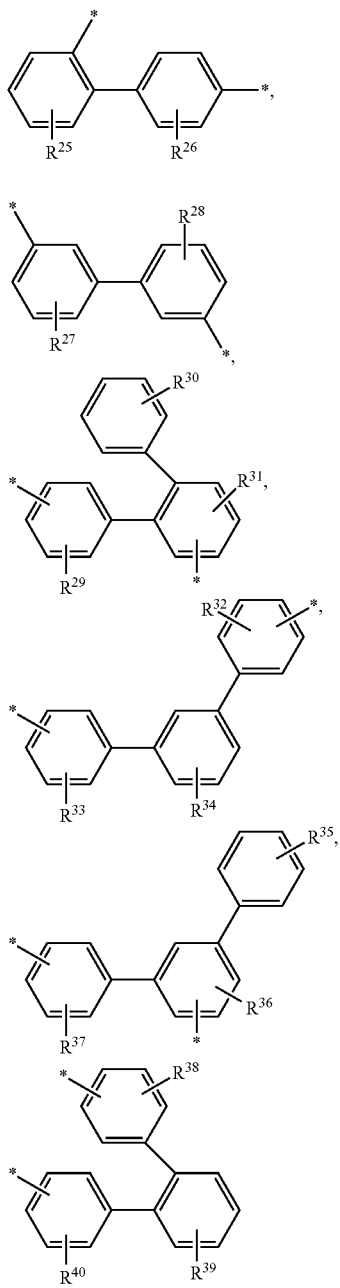

wherein, in Group 1,
R[13] to R[40] are independently hydrogen, deuterium, a substituted or unsubstituted C1 to C10 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a halogen, a halogen-containing group, a cyano group, a hydroxyl group, an amino group, a nitro group, a carboxyl group, a ferrocenyl group or a combination thereof.

10. An organic compound listed in Group 2:

[Group 2]

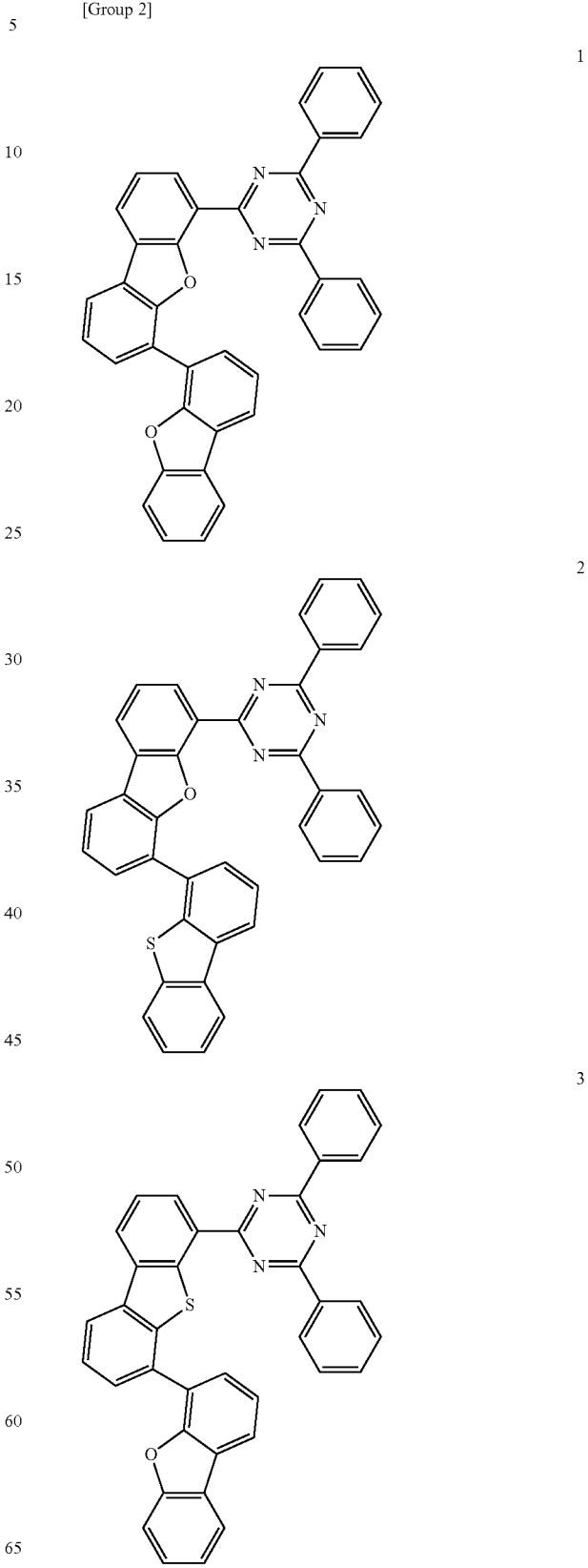

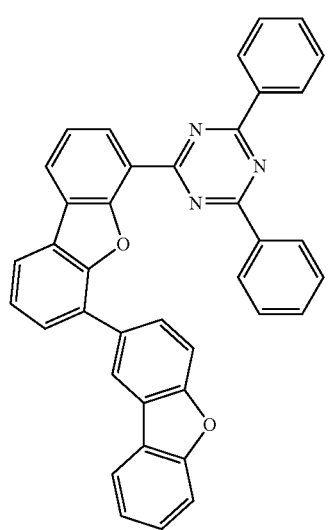
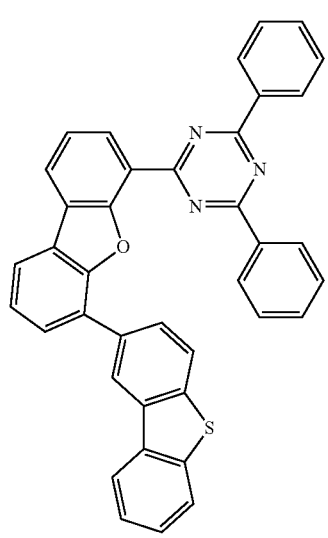
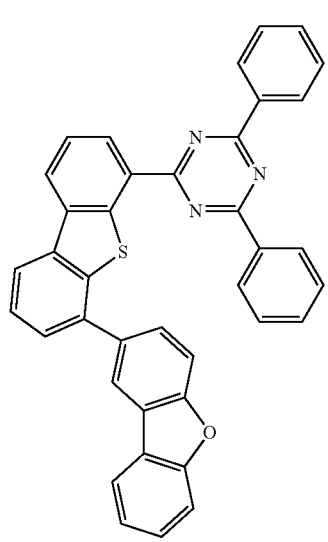
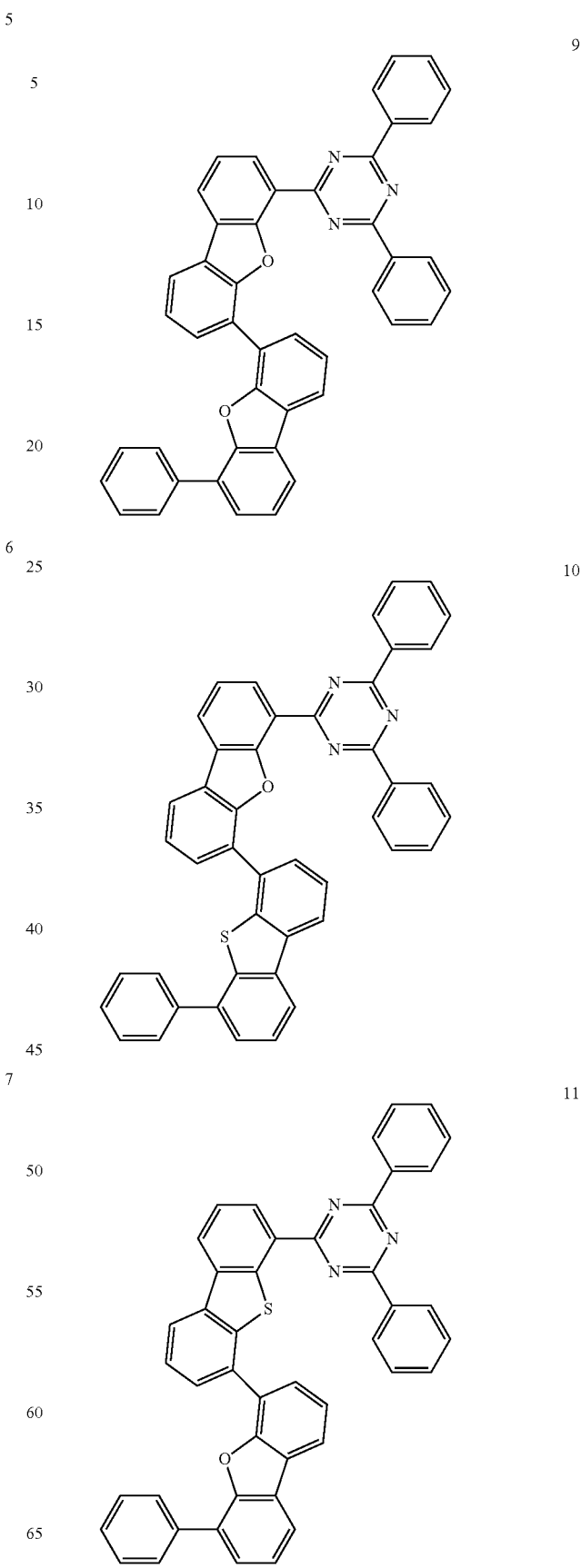

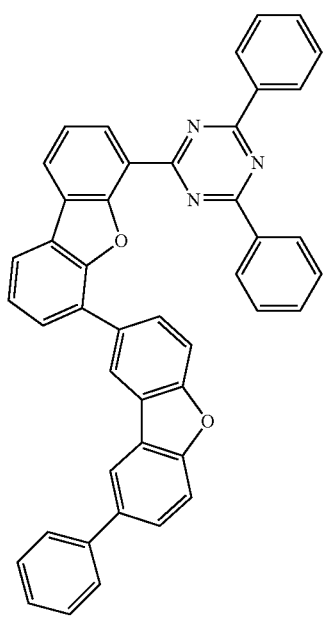
13
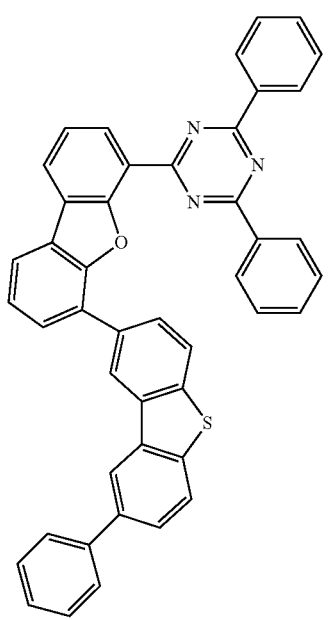
14
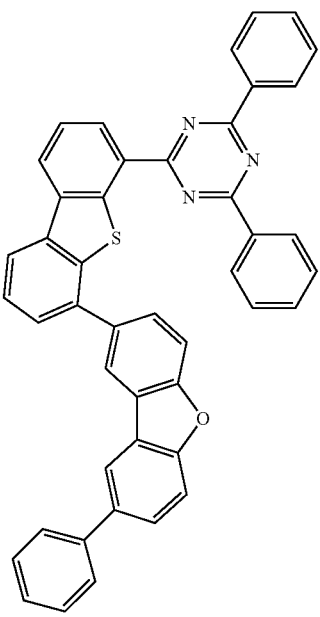
15
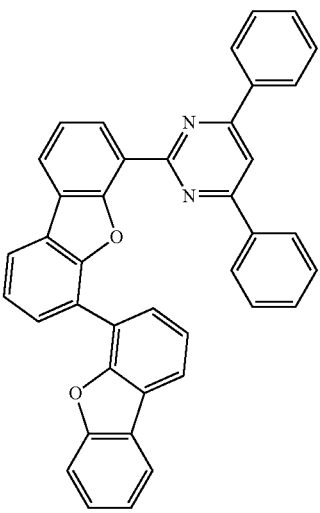
17
18

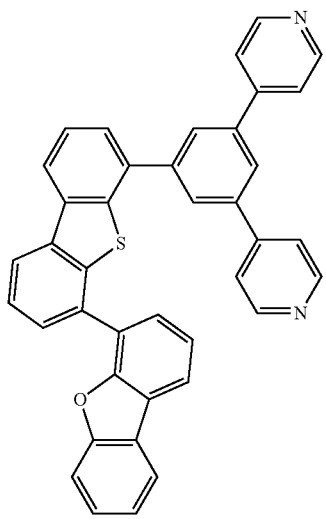
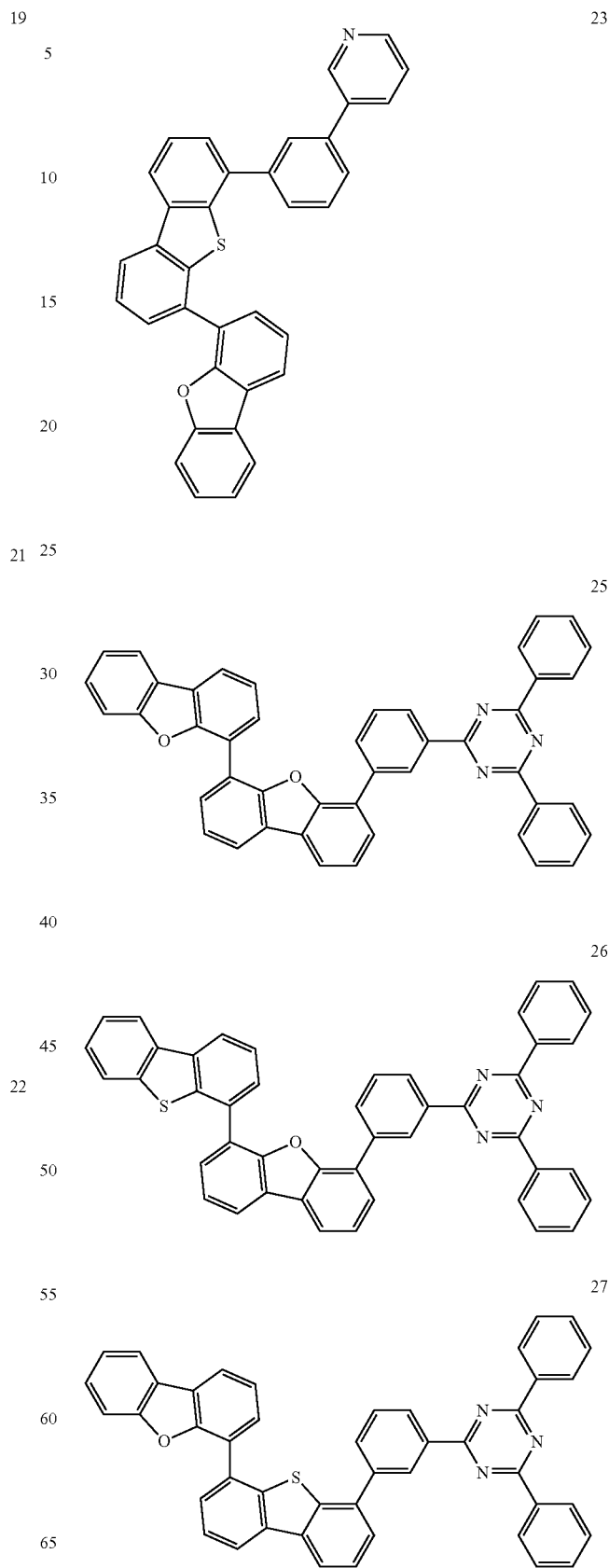

29
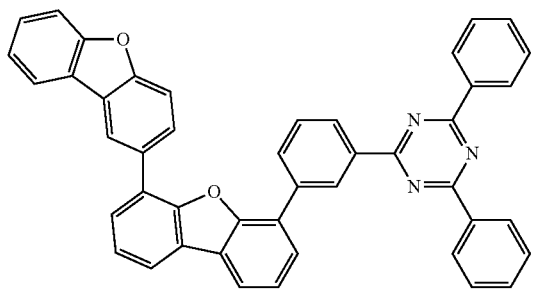
30
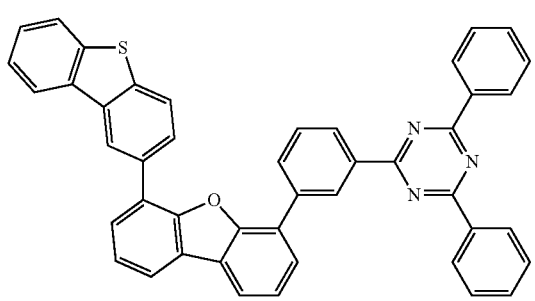
31
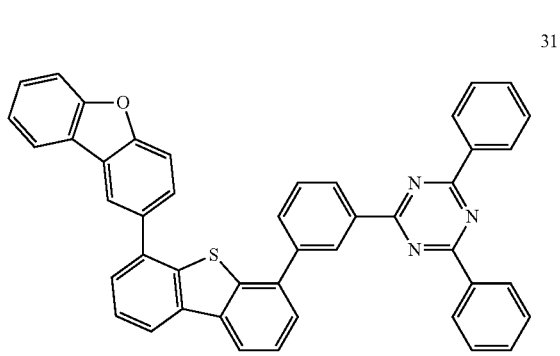 [SMILES: c1ccc(-c2nc(-c3ccccc3)nc(-c3cccc(-c4cccc5c4sc4c(-c6ccc7oc8ccccc8c7c6)cccc45)c3)n2)cc1]
33
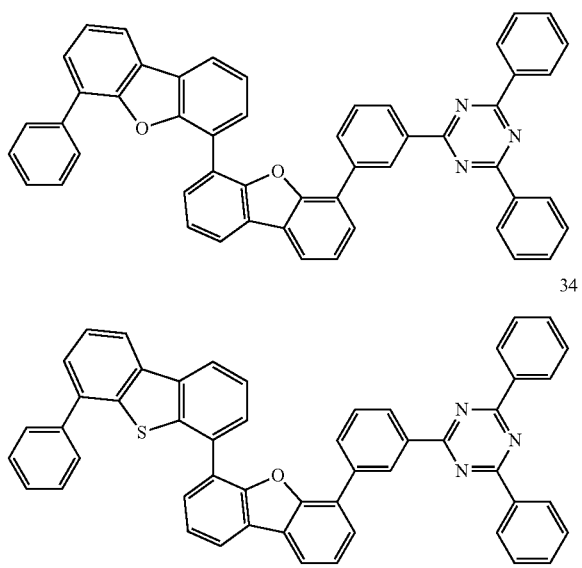
34
35
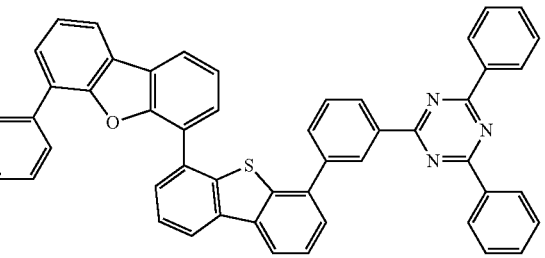
37
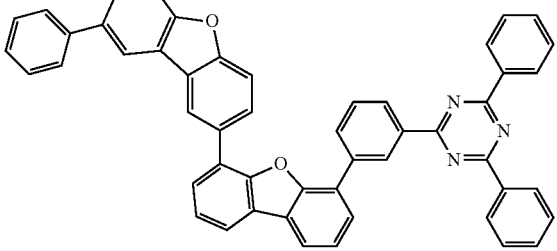
38
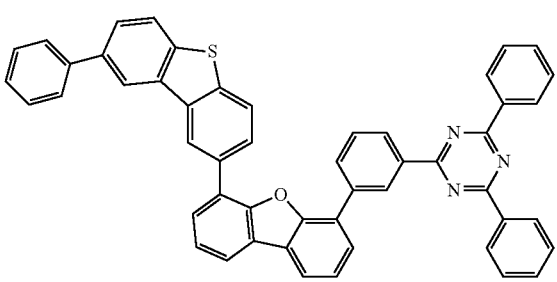
39
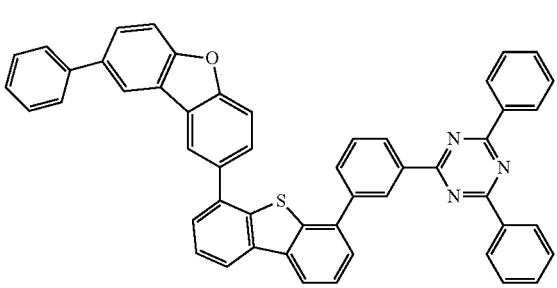
41
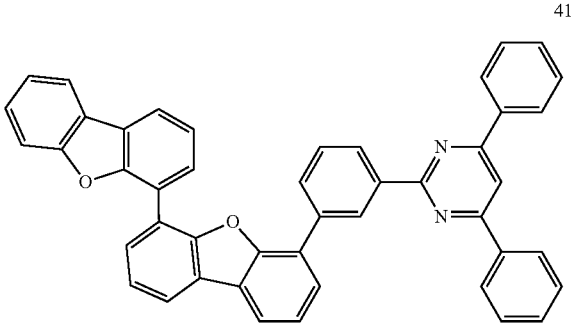 [SMILES: c1ccc(-c2cc(-c3cccc(-c4cccc5c4sc4c(-c6cccc7c6oc6ccccc67)cccc45)c3)cc(-c3ccccn3)c2)nc1]

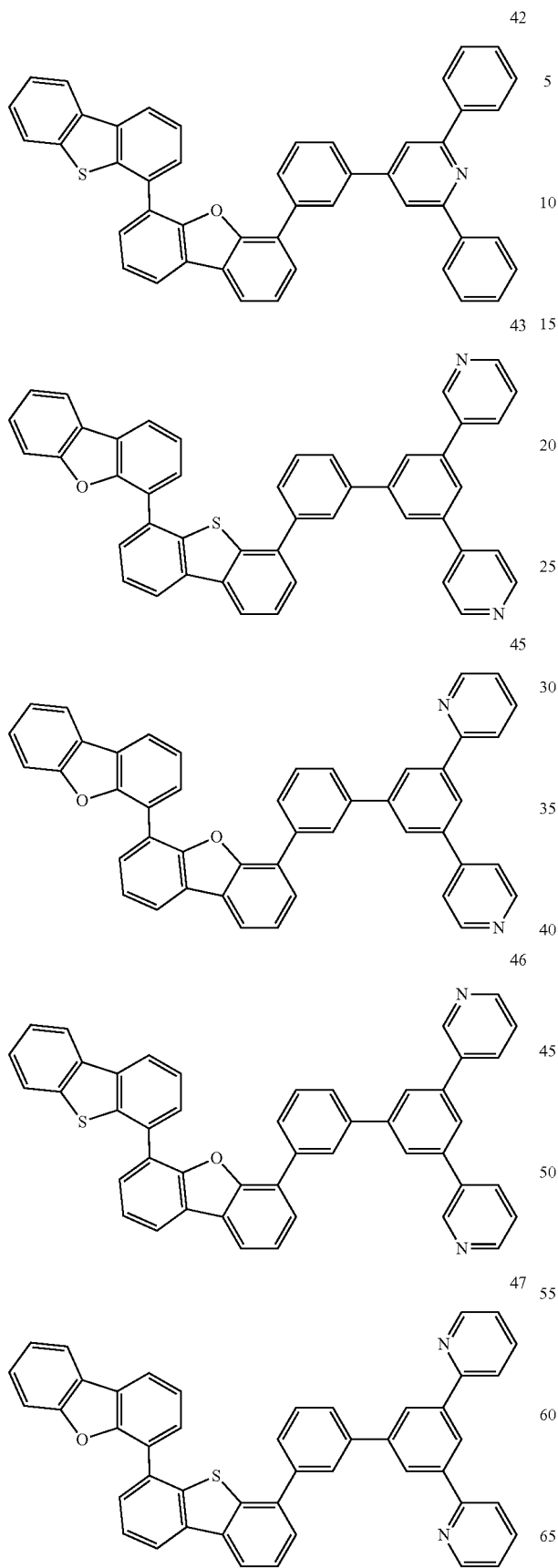
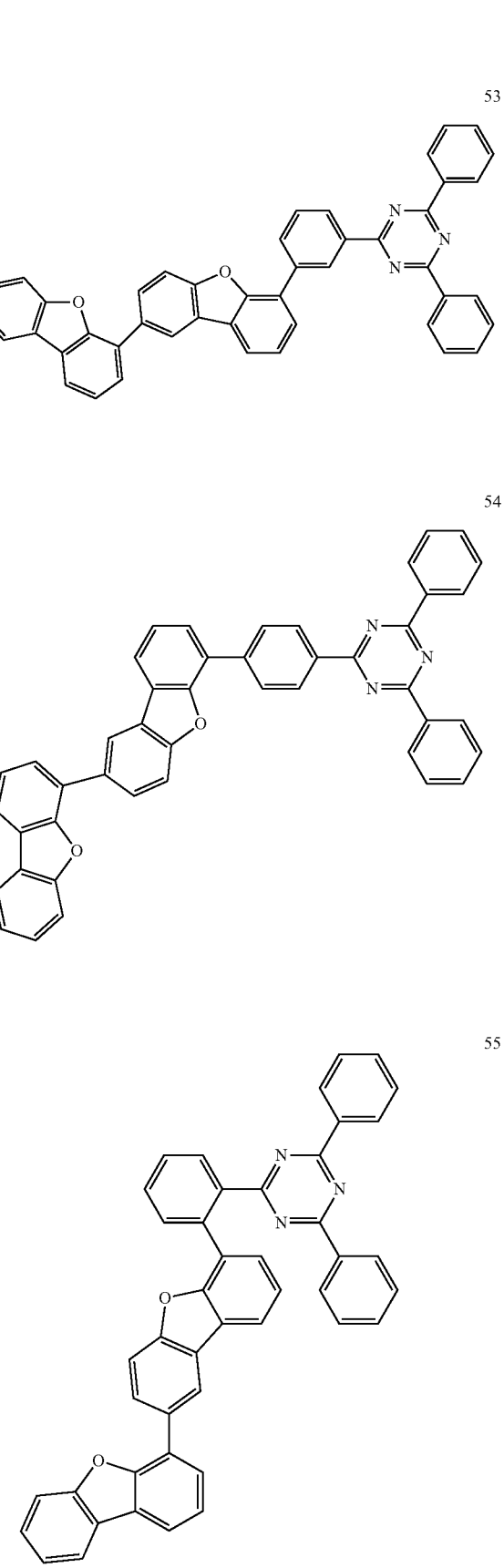

56
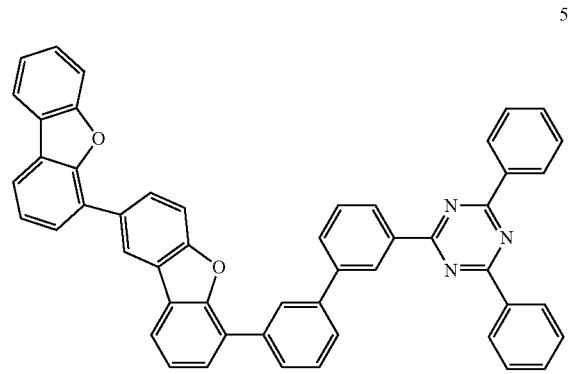
57
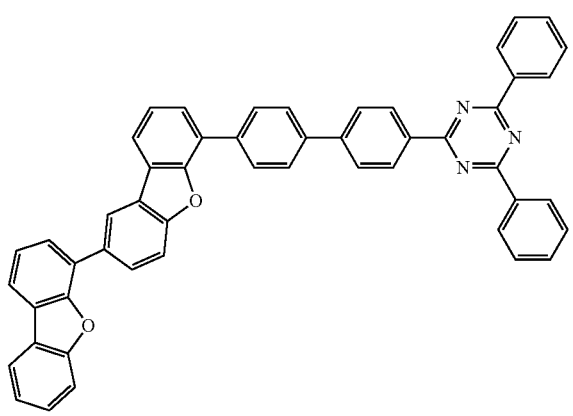
58
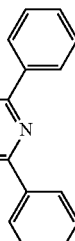
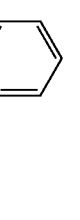
59
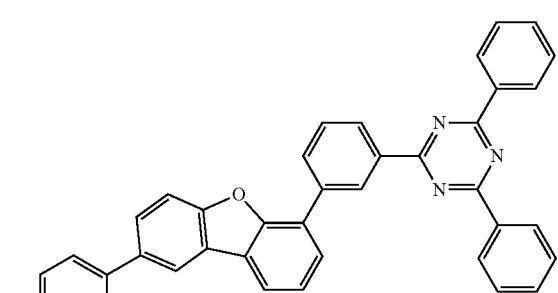
61
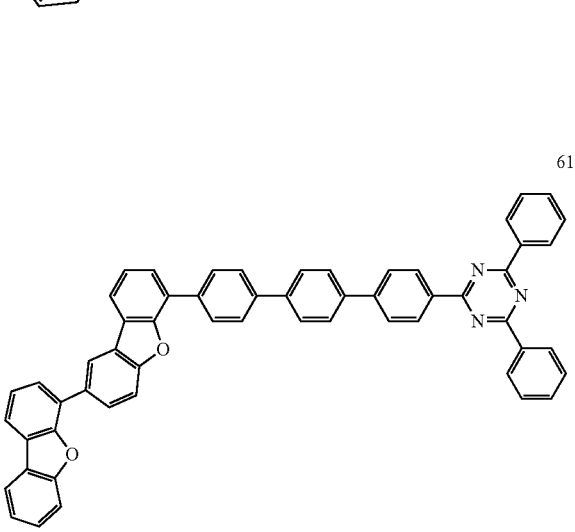
62
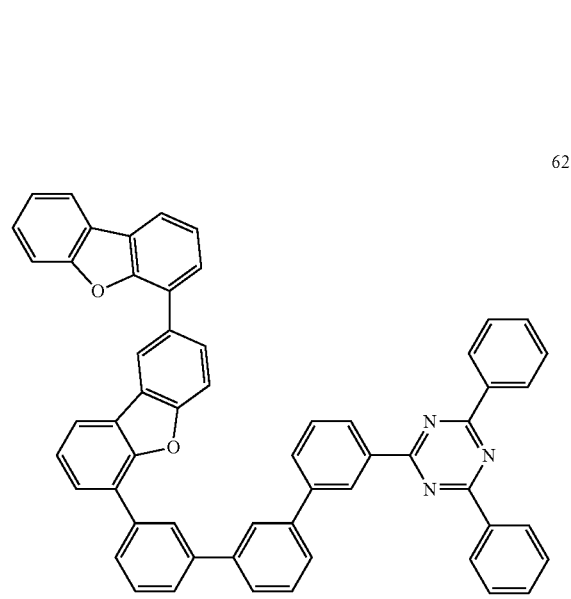

-continued

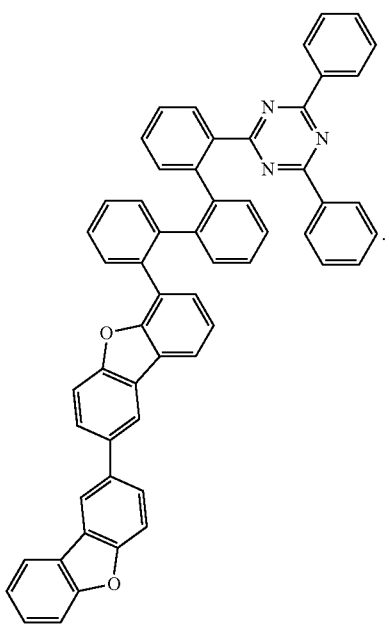

11. An organic optoelectronic device, comprising
an anode and a cathode facing each other,
at least one organic layer between the anode and the cathode,
wherein the organic layer comprises the organic compound of claim 1.

12. The organic optoelectronic device of claim 11, wherein the organic layer comprises an emission layer, and the emission layer comprises the organic compound.

13. The organic optoelectronic device of claim 12, wherein the organic compound is included as a host of the emission layer.

14. The organic optoelectronic device of claim 11, wherein the organic layer comprises at least one selected from a hole injection layer, a hole transport layer, an electron blocking layer, an electron transport layer, an electron injection layer, and a hole blocking layer.

15. A display device comprising the organic optoelectronic device of claim 11.

16. An organic optoelectronic device, comprising:
an anode and a cathode facing each other,
at least one organic layer between the anode and the cathode,
wherein the organic layer comprises an organic compound listed in Group 2 of claim 10.

17. A display device comprising the organic optoelectronic device of claim 16.

* * * * *